US006987007B2

(12) United States Patent
Xu et al.

(10) Patent No.: US 6,987,007 B2
(45) Date of Patent: Jan. 17, 2006

(54) MODIFIED CHITIN-BINDING DOMAIN AND USE THEREOF

(75) Inventors: Ming-Qun Xu, Hamilton, MA (US); Sebastien M. Ferrandon, Oxford (GB)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 11/110,002

(22) Filed: Apr. 20, 2005

(65) Prior Publication Data

US 2005/0196841 A1 Sep. 8, 2005

Related U.S. Application Data

(62) Division of application No. 10/375,913, filed on Feb. 26, 2003, now Pat. No. 6,897,285.

(60) Provisional application No. 60/360,354, filed on Feb. 28, 2002.

(51) Int. Cl.
*C12P 21/00* (2006.01)

(52) U.S. Cl. .................... 435/69.7; 435/200; 530/300; 530/350; 514/12

(58) Field of Classification Search ............... 435/69.1, 435/69.7; 530/300, 350; 514/12
See application file for complete search history.

(56) References Cited

U.S. PATENT DOCUMENTS

| 5,187,262 A | 2/1993 | Raikhel et al. |
|---|---|---|
| 5,643,758 A | 7/1997 | Guan et al. |
| 5,834,247 A | 11/1998 | Comb et al. |
| 5,928,917 A | 7/1999 | Kilburn et al. |
| 5,962,289 A | 10/1999 | Kilburn et al. |
| 6,124,117 A | 9/2000 | Kilburn et al. |
| 6,174,700 B1 | 1/2001 | Haynes et al. |

FOREIGN PATENT DOCUMENTS

| WO | WO 00/47751 | 8/2000 |
|---|---|---|
| WO | WO 01/57183 | 8/2001 |

OTHER PUBLICATIONS

Yamagami et al. Biosci Biotech. Biochem. 61(11): 1819-1825 (1997).*
LaVallie and McCoy, Curr. Opin. Biotechnol., 6501-506 (1995).
Xu, et al., Methods Enzymol. 326:376-418 (2000).
Van Dyke, et al. Gene 111:99-104 (1992).
Smith and Johnson, Gene 67:31-40 (1998).
Watanabe, et al., J. Bacteriol. 176:4465-4472 (1994).
Jolles, et al. Chitin and Chitinases, Birkhauser Verlag, Basel (1999).
Hashimoto, et al. J. Bacteriol. 182:3045-3054 (2000).
Watanabe, et al. J. Bacteriol. 172:4017-4022 (1990).
Alam, et al. J. Ferment. Bioeng. 82:28-36 (1996).
Nagai, et al., Nature 309:810-812 (1984).
New England Catalog 2002/2003, p. 163.
Steel, et al. J. Immunol. 145:3917-3923 (1990).
Evans, et al., Biopolymers 51:333-342 (1999a).
Cantrell, et al. Proc. Natl. Acad. Sci, USA 82:6250-6254 (1985).
Mingsheng, et al., J. Biotechnol. 11:157-162 (1995).
Evans, et al. J. Biol. Chem. 274:18359-18363 (1999b).
Yamamoto, et al., Nature 319:230-234 (1986).
Doherty, et al., Proc. Natl. Acad. Sci. USA 96:10869-10874 (1999).
Chong, et al., Gene 192:271-281 (1997).
Studier, et al., Methods Enzymol. 185:60-89 (1990).
Bradford, Anal. Biochem., 72:248-254 (1976).
Ikegami et al., Solution Structure of the Chitin-binding Domain of *Bacillus circulans* WL-12 Chitinase A1, The Journal of Biological Chemistry, vol. 275, No. 18:13654-13661(2000).
Boller et al., Chitinase in Bean Leaves:Induction by Ethylene, Purification, Properties, and Possible Function, Planta, vol. 157:22-31 (1983).

* cited by examiner

*Primary Examiner*—Karen Cochrane Carlson
*Assistant Examiner*—Anand Desai
(74) *Attorney, Agent, or Firm*—Harriet M. Strimpel

(57) ABSTRACT

Compositions and methods are provided for reversibly binding chitin binding domain (CBD) to a chitin or equivalent substrate under non denaturing conditions. CBD is modified preferably by a mutation to achieve this change in properties. In one embodiment, an aromatic amino acid residue located in the binding cleft of the CBD was altered resulting in reversible binding affinity for substrate in select conditions. Creating a modified CBD with an altered binding affinity for substrate provides new uses for CBD not previously possible with unmodified CBD which binds irreversibly to chitin.

7 Claims, 10 Drawing Sheets

W 687 T

P 689 F

MODIFIED CHITIN-BINDING DOMAIN AND USE THEREOF

CROSS REFERENCE

This Application is a divisional application of U.S. application Ser. No. 10/375,913 filed Feb. 26, 2003, U.S. Pat. No. 6,897,285, which gains priority from Provisional Application Ser. No. 60/360,354 filed Feb. 28, 2002, each of which is herein incorporated by reference.

BACKGROUND

The present invention relates to a modified chitin binding domain and methods for making the same where the modification alters the properties of the chitin binding domain so that it becomes capable, under select conditions, of elution from a substrate for which it has specific affinity.

Although a number of different approaches to protein purification exist, the application of recombinant techniques to generating fusion proteins from target proteins and substrate binding proteins (affinity tags) has provided efficient methods of separating target proteins from complex mixtures and/or large volumes. (LaVallie and McCoy, Curr. Opin. Biotechnol., 6:501–506 (1995), U.S. Pat. Nos. 5,834,247 and 5,643,758). Examples of substrate binding proteins include the chitin binding domain (CBD or ChBD) of chitinase which binds chitin substrate (U.S. Pat. No. 5,837,247, Xu et al., Methods Enzymol. 326:376–418 (2000)), maltose binding protein which binds an amylose substrate (U.S. Pat. No. 5,643,758), cellulose binding domain from cellulase which binds cellulose (U.S. Pat. Nos. 5,962,289; 5,928,917; and 6,124,177) and His-Tag (an oligopeptide) which binds a Nickel charged column. (Van Dyke, et al. Gene 111:99–104 (1992)). In addition to the above, Glutathione S-transferase (GST) bind sepharose TM4B resin (Smith, D. B., and Johnson, K. S. Gene 67:31–40 (1998)).

Each of the above affinity tags has certain limitations. For example, CBD irreversibly binds to chitin substrate and cannot be eluted under non-denaturing conditions. However, CBD represents a potentially useful affinity tag with widespread application since it is readily obtained from any of a family of enzymes identified as chitinases that are capable of hydrolyzing chitin. As might be expected, chitinases are produced by a diverse range of organisms that either contain chitin or rely on chitin as a food source. These organisms include bacteria, fungi, plants and vertebrates. (Watanabe et al. J. Bacteriol., 176:4465–4472 (1994), Jolles et al., Chitin and Chitinases, Birkhäuser Verlag, Basel (1999); Hashimoto et al., J. Bacteriol. 182:3045–3054 (2000)). CBD binds to chitin, a polysaccharide abundantly represented in nature. It is found in many fungal cell walls, nematode and insect exoskeletons, and crustacean shells.

Chitinases are characterized by a chitin binding domain (CBD) and a catalytic domain. For example, Chitinase A1 which is produced by Bacillus circulans WL-12 contains three discrete functional domains: an N-terminal family 18 catalytic domain, a tandem repeat of fibronectin type III-like domains and a C-terminal chitin-binding domain (FIG. 1) (Watanabe et al., supra (1994)). Moreover, since CBD is located within the chitinase at a site that is distinct from the catalytic domain, it naturally lacks hydrolytic activity when isolated from the enzyme for use as an affinity tag.

While CBD has a number of useful properties it lacks the property of reversible binding to chitin under non-denaturing conditions which limits its general utility.

SUMMARY OF THE INVENTION

In an embodiment of the invention, a protein is provided that includes a chitin binding domain (CBD) capable of reversibly binding a chitin substrate under selected non denaturing conditions. The chitin binding domain may be modified by having one or more mutated amino acids. The mutated amino acid may be an aromatic amino acid optionally positioned within a binding cleft of the CBD, for example, a tryptophan. In a particular embodiment, the tryptophan corresponds to Trp 687 of B. circulans chitinase A2.

Selected conditions for reversibly binding a chitin binding domain include a change in one of: ionic concentration, pH, detergent concentration, antagonist or agonist concentration. For example a change in ionic conditions may include a reduction in salt conditions.

In an additional embodiment of the invention, a method is provided for obtaining a chitin binding domain capable of reversible binding to a chitin substrate under non-denaturing conditions where the method includes the steps of modifying at least one amino acid within the CBD, and determining whether the modified CBD is capable of reversibly binding chitin under selected conditions. One type of modification is a mutation of a portion of DNA sequence encoding the CBD followed by expression of the DNA in a host cell. The mutation may be introduced into the portion of the DNA sequence by substituting an existing oligonucleotide portion of the DNA sequence with an alternative oligonucleotide which differs in that it contains a mutation at a target site. For example, the target site may be a tryptophan located in the binding cleft of the CBD. When for example, the tryptophan is substituted with a phenylalanine, the CBD is capable of reversible binding to chitin under non-denaturing conditions. For example, non-denaturing conditions include a change in any of: ionic concentration; pH; detergent concentration; or antagonist or agonist concentration.

In an additional embodiment of the invention, a method is provided for producing and purifying a target protein molecule where the method includes the steps of: constructing a DNA expression vector which expresses a hybrid polypeptide in a transformed host cell, the hybrid polypeptide comprising the target protein molecule and a modified chitin binding domain where the chitin binding domain has a specific and reversible affinity for a substrate such as chitin or derivatives or analogues thereof; introducing the expression vector into an appropriate host cell; expressing the hybrid polypeptide; contacting the hybrid polypeptide produced by the transformed cell with the substrate to which the CBD binds; and recovering the hybrid polypeptide. The hybrid polypeptide may for example be recovered from the substrate to which it is bound by altering the ionic condition or pH or by contacting the bound hybrid polypeptide with a detergent or an agonist or antagonist which displaces the hybrid polypeptide.

In an additional embodiment of the invention, a method is provided for purifying a chitin binding domain-target molecule conjugate from a mixture of molecules. The method includes the steps of adding to the mixture, a substrate having a specific and reversible affinity for CBD so as to permit binding and immobilizing of the conjugate to the substrate; removing the bound conjugate from the mixture; and eluting in altered ionic conditions, the conjugate from the substrate to obtain the purified conjugate.

In an additional embodiment of the invention, a kit is provided for purifying a recombinant protein, that includes a plasmid, the plasmid containing a DNA sequence encoding a modified CBD or portion thereof and an insertion site for inserting the DNA sequence encoding the recombinant protein; a substrate for specific and reversible binding of the fusion protein; and optionally a buffer for eluting the fusion protein from the substrate.

In an embodiment of the invention, a vector within or separate from a host cell is provided where the vector is capable of expressing a modified chitin binding domain (CBD) fused to a protein molecule to be purified, the vector including a DNA fragment coding for the modified chitin binding domain or portion thereof, having a specific and reversible affinity for a substrate which binds to the chitin binding protein. The vector may further express an additional DNA fragment coding for the protein molecule to be purified where the additional DNA fragment is optionally located within or adjacent to the CBD sequence.

BRIEF DESCRIPTION OF THE DRAWINGS

FIG. 2. Schematic ribbon drawing of the CBD of *Bacillus circulans* chitinase A1.

FIG. 3. Chitin binding activity of PXB mutant proteins. The mutated CBD was expressed as a fusion protein (PXB, 56 kDa) consisting of the N-terminal paramyosin ΔSal fragment (P, 26 kDa), the Mxe GyrA mini-intein (X, 22 kDa) and the mutated CBDof *Bacillus circulans* chitinase A1 (B, 8 kDa).

The samples were analyzed by Coomassie Blue stained SDS-PAGE. The mutated amino acid and its position in the CBD are indicated on top of each gel. UI, uninduced cell extract. Lanes 1 and 4, clarified cell extract. Lanes 2 and 4, chitin flow-through. Lanes 3 and 6, a sample of chitin beads following wash with the same buffer used for loading. Broad Range protein marker (kDa) is indicated on the left side of each gel.

Figure 4A:
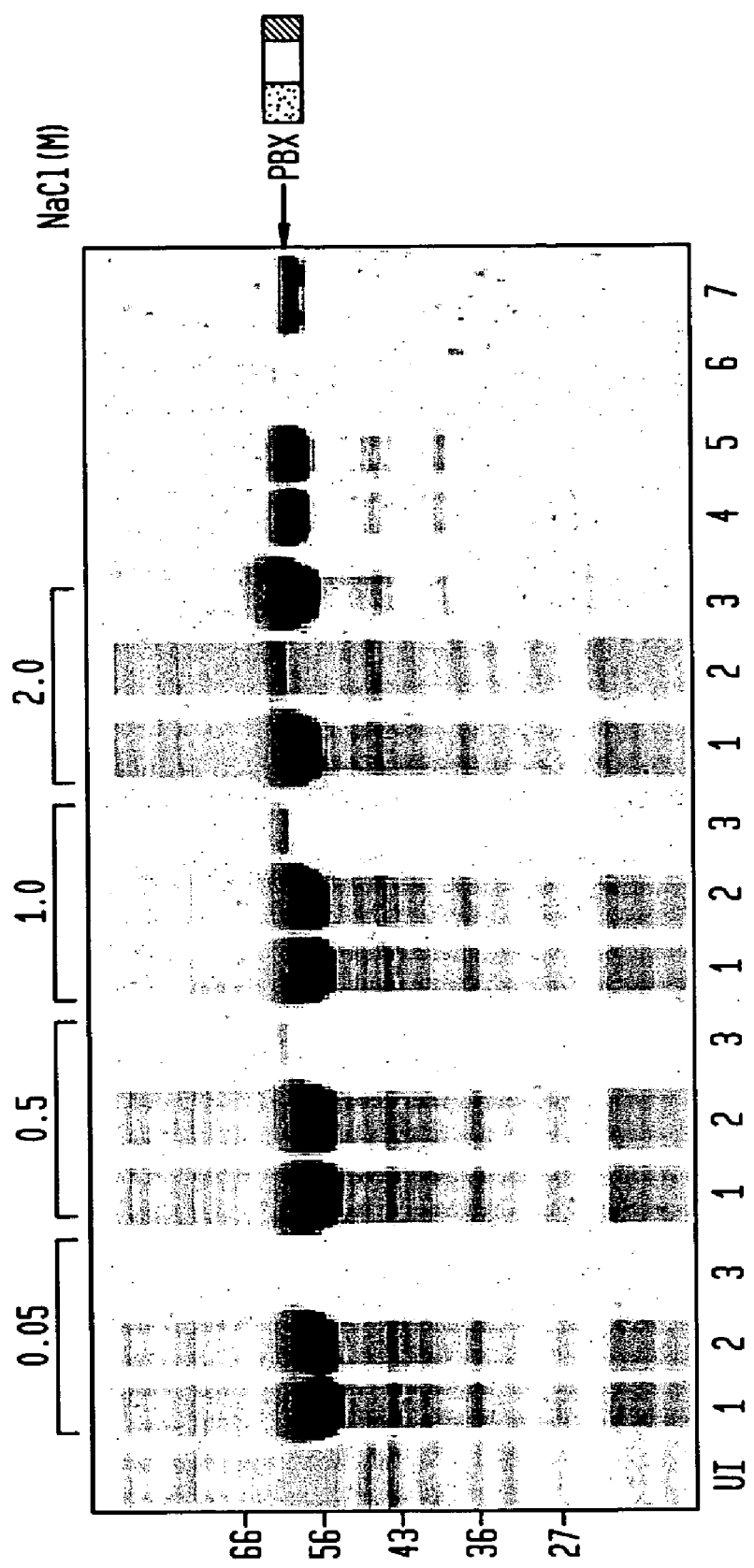

FIG. 4A. Characterization of the W687F mutant. Chitin binding activity of PXB W687F mutant protein at various NaCl concentrations. Induced cells were lysed in 20 mM Tris-buffer (pH 8) containing various NaCl concentrations indicated at the top of the gel. The samples were analyzed by Coomassie Blue stained SDS-PAGE. UI, uninduced cell extract. Lane 1, crude cell extract. Lane 2, flow-through. Lane 3, a sample of chitin beads following wash with the appropriate buffer. Lanes 4 and 5, a fraction after elution with buffer containing 50 mM or no NaCl following loading and washing with buffer containing 2 M NaCl. Lane 6, a sample after passage of the eluted fraction adjusted to 2 M NaCl over a new chitin resin. Lane 7, a sample of chitin beads after reloading and washing with a buffer containing 2 M NaCl.

Figure 4B:
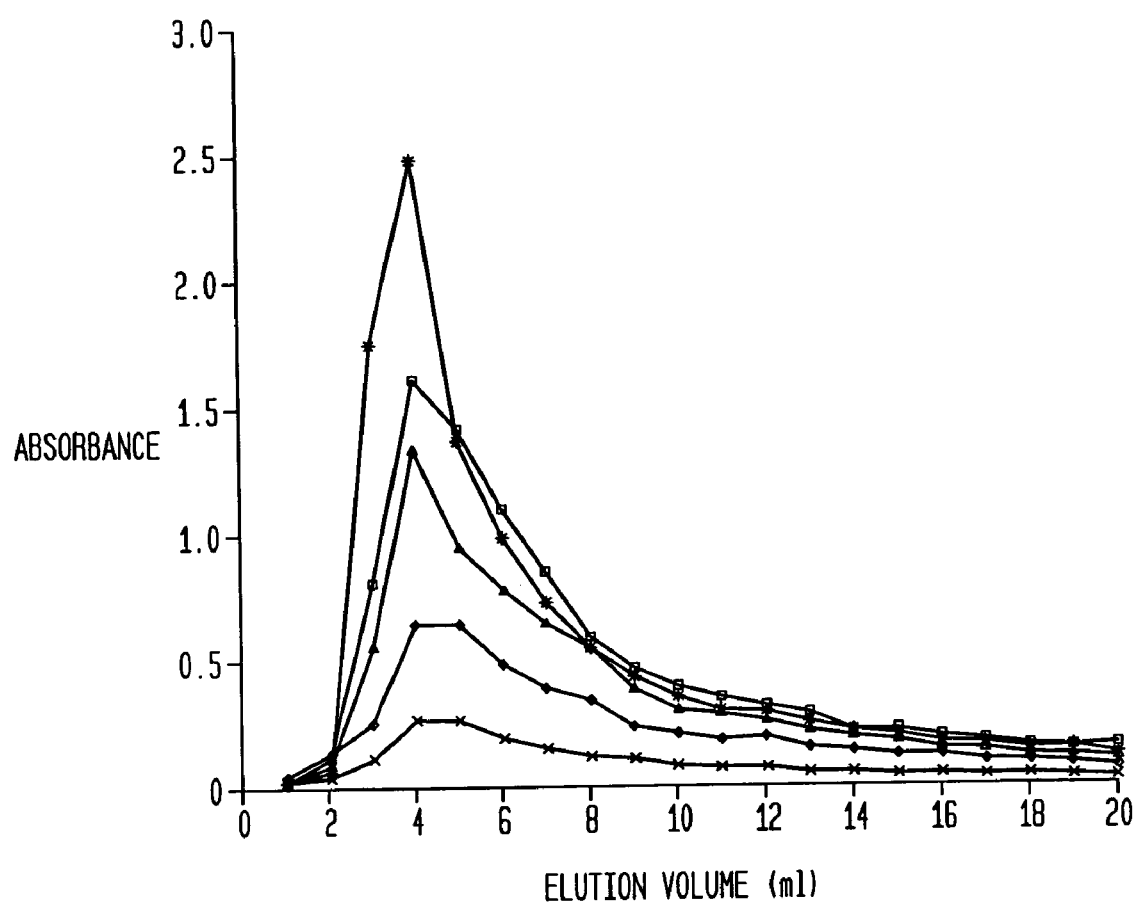

FIG. 4B. Elution curves of PXB W687F mutant at different salt concentrations. Loading of the wild type PXB protein and of the W687F mutant was carried out at 2 M NaCl. For the PXB W687F mutant, elutions were achieved in 20 mM Tris (pH 8) containing either 50 mM NaCl (♦), 0.1 M NaCl (□), 0.5 M NaCl (▲), or 1 M NaCl (O). The elution of the wild type PXB was performed at 50 mM NaCl (X).

FIG. 5. Purification of recombinant proteins fused to the ChBD carrying the W687F mutation.

Figure 5A:
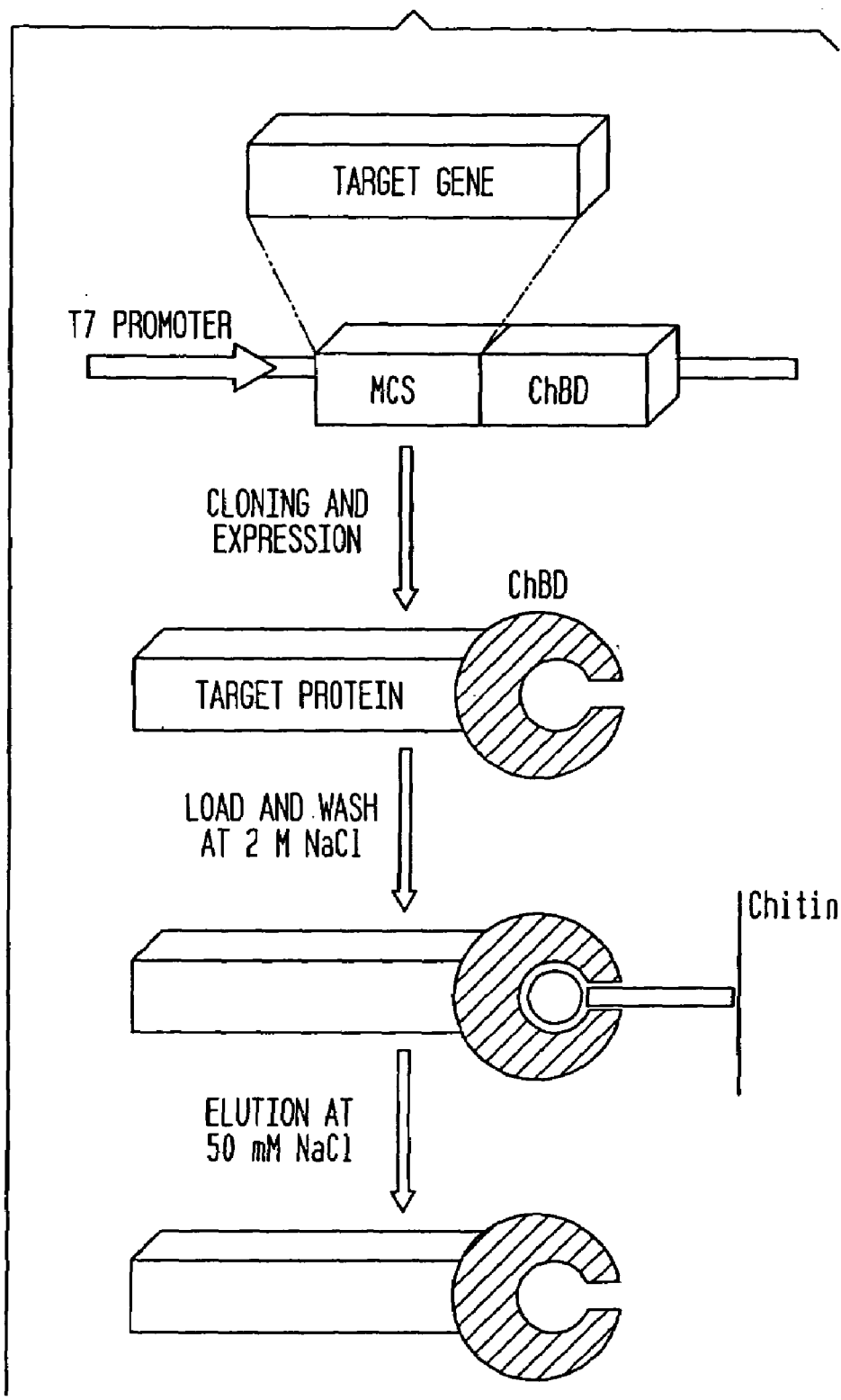

FIG. 5A. Schematic overview of the one-step affinity purification for recombinant proteins fused to the CBD (W687F).

Figure 5B:
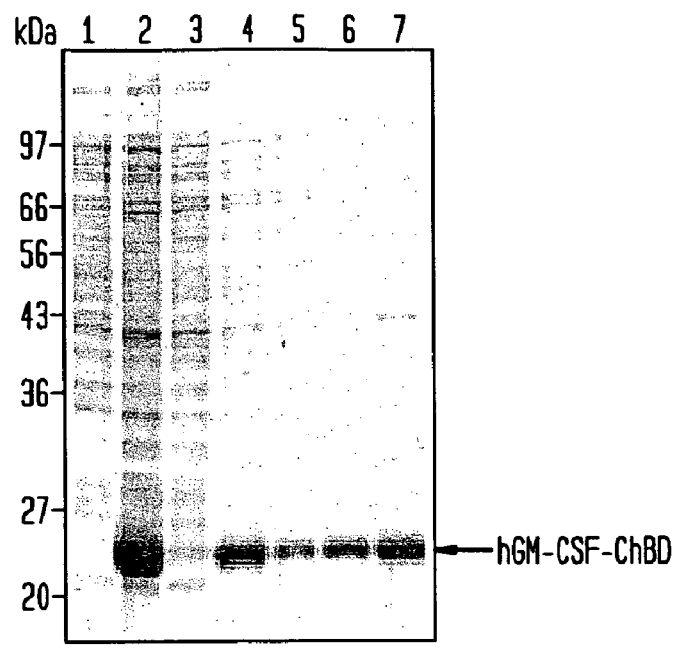

FIG. 5B. Purification of hGM-CSF-ChBD.

Figure 5C:
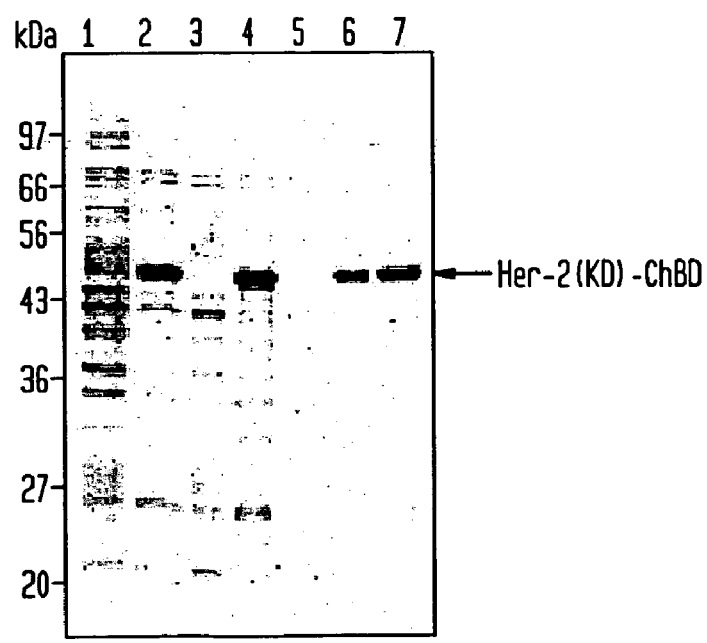

FIG. 5C. Purification of Her-2(KD)-ChBD.

The samples were analyzed by Coomassie Blue stained SDS-PAGE. Lane 1, uninduced cell extract. Lane 2, crude cell extract. Lane 3, supernatant from the crude cell extract after centrifugation. Lane 4, load of renatured proteins in 20 mM Tris buffer (pH 8) containing 2 M NaCl. Lane 5, renatured proteins flow-through. Lane 6, a sample of chitin beads after loading renatured proteins. Lane 7, eluted protein from chitin beads with 20 mM Tris-buffer (pH 8) containing 50 mM NaCl.

DETAILED DESCRIPTION OF THE EMBODIMENTS

The utility of CBD has been enhanced by modifications to the protein that cause the CBD to be capable of reversible binding to a chitin substrate under conditions that do not denature proteins (non-denaturing conditions).

The modified CBD may be linked to a protein or other molecule of interest whether covalently or by affinity binding or via a linker molecule to form a molecular conjugate. Where the conjugate is present in a mixture, it may be selectively bound to a CBD-specific substrate and eluted from the substrate under select conditions.

Figure 1:
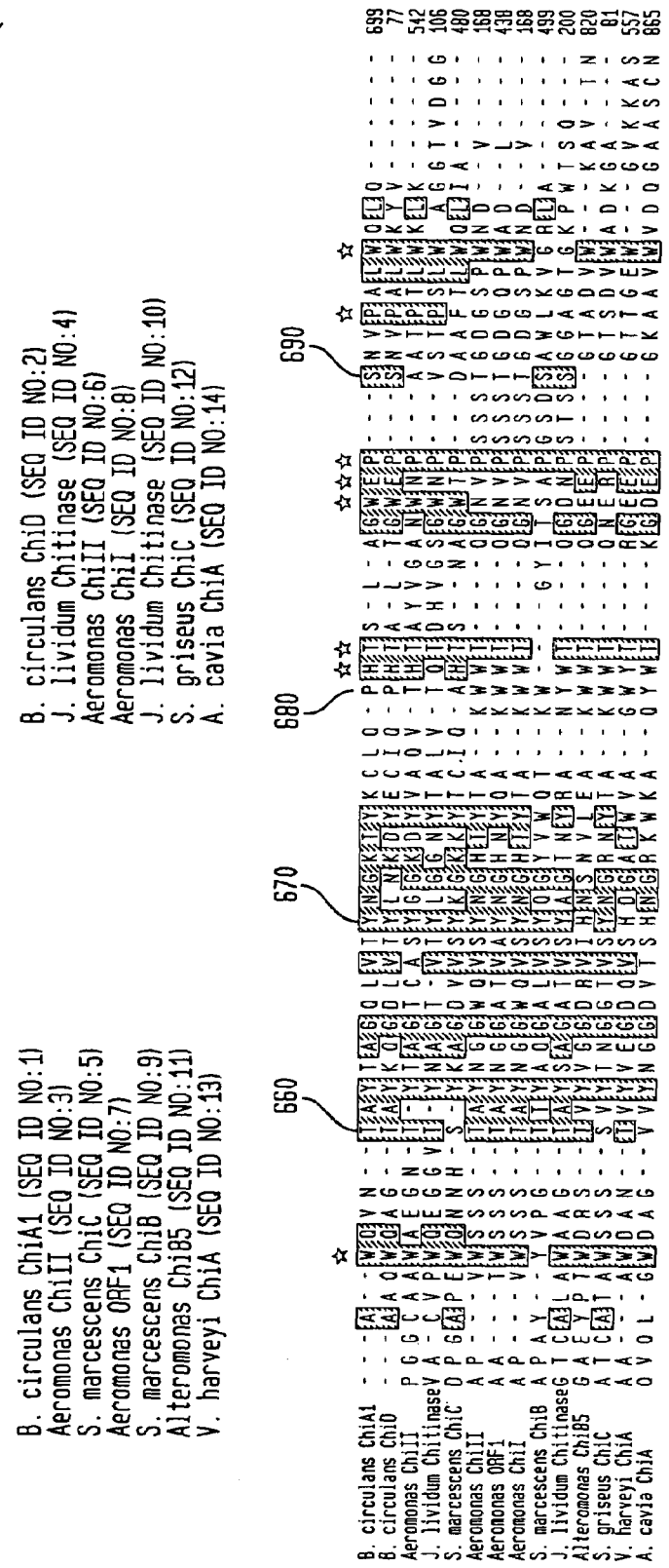
FIG. 1. Amino acid sequence alignment of the chitin-binding domain from *Bacillus circulans* chitinase A1 with domains of other procaryotic chitinases. Sequences were aligned with the program CLUSTAL V (40). Conserved residues are indicated in black boxes. Amino acids sequences shown are from: CBD of *Bacillus circulans* WL-12 chitinase A1 (*B. circulans* A1 (SEQ ID NO:1)), *Bacillus circulans* WL-12 chitinase D (*B. circulans* ChiD (SEQ ID NO:2)), *Aeromonas* sp. Strain 10S-24 chitinase II (*Aeromonas* ChiII (SEQ ID NO:3)), *Janthinobacterium lividum* chitinase (*J. lividum* Chitinase (SEQ ID NO:4)), *Serratia marcescens* 2170 chitinase C(*S. marcescens* ChiC (SEQ ID NO:5)), *Aeromonas* sp. Strain 10S-24 chitinase II (*Aeromonas* ChiII (SEQ ID NO:6)), *Aeromonas* sp. Strain 10S ORF1 (*Aeromonas* ORF1 (SEQ ID NO:7)), *Aeromonas* sp. Strain 10S-24 chitinase I (*Aeromonas* ChiI (SEQ ID NO:8)), *Serratia marcescens* 2170 chitinase B (*S. marcescens* ChiB (SEQ ID NO:9)), *Janthinobacterium lividum* chitinase (*J. lividum* Chitinase (SEQ ID NO:10)), *Alteromonas* sp. Strain 0-7 chitinase 85 (*Alteromonas* Chi85 (SEQ ID NO:11)), *Streptomyces griseus* chitinase C(*S. griseus* ChiC (SEQ ID NO:12)), *Vibrio harveyi* chitinase A (*V. harveyi* ChiA (SEQ ID NO:13)), *Aeromonas caviae* extracellular chitinase A (*A. cavia* ChiA (SEQ ID NO:14)). The first five sequences are considered to belong to the $CBD_{ChiA1}$ group. The number at the right of each sequence represents the position of the last residue in each sequence. The residues of $CBD_{ChiA1}$ that were mutated, are indicated by a star above the sequence. The numbers at the top represent the position in *B. circulans* ChiA1.

"Chitin binding domain", "CBD" or ChBD here refers to any binding domain derived from a naturally occurring or recombinant chitinase, including chitinases for which sequences are available from sequence databases such as GenBank to or contained within gene libraries made according to standard molecular biology techniques (Sambrook et al., Molecular Cloning: A Laboratory Manual, CSH 1989) using conserved sequence motifs such as described in FIG. 1. FIG. 1 provides an example of sequence motifs observed when 13 chitin binding domains from different sources were aligned. Examples of chitinases include at least 6 different chitinases, A1, A2, B1, B2, C, and D present in *Bacillus circulans* WL-12 (Watanabe et al., *J. Bacteriol.*, 172:4017–4022 (1990); Watanabe et al., *J. Bacteriol.*, 176: 4465–4472 (1994)) derived from four genes, chiA, chiB, chiC, and chiD, with chitinase A2 and B2 being generated by proteolytic modification of chitinase A1 and B1, respectively (Alam et al., *J. Ferment. Bioeng.*, 82:28–36 (1996)).

A "target molecule" is a molecule of interest that includes any prokaryotic or eukaryotic, simple or conjugated protein that can be expressed by a vector in a transformed host cell and further includes proteins that may be subject to post translational modifications in natural or synthetic reactions.

The term "protein" is intended to include peptides and derivatives of proteins or peptides and to further include portions or fragments of proteins and peptides. Examples of proteins include enzymes including endonucleases, methylases, oxidoreductases, transferases, hydrolases, lyases, isomerases or ligases, storage proteins, such as ferritin or ovalbumin; transport proteins, such as hemoglobin, serum albumin or ceruloplasmin; structural proteins that function in contractile and motile systems, for instance, actin, myosin, fibrous proteins, collagen, elastin, alpha-keratin, glycoproteins, virus-proteins and muco-proteins; immunological proteins such as antigens or antigenic determinants which can be used in the preparation of vaccines or diagnostic reagents; blood proteins such as thrombin and fibrinogen; binding proteins, such as antibodies or immunoglobulins that bind to and thus neutralize antigens; hormones and factors such as human growth hormone, somatostatin, prolactin, estrone, progesterone, melanocyte, thyrotropin, calcitonin, gonadotropin, insulin, interleukin 1, intereukin 2, colony stimulating factor, macrophage-activating factor and interferon; toxic proteins, such as ricin from castor bean or grossypin from cotton linseed and synthetic proteins or peptides.

It is further envisioned that in addition to a protein expressed by a vector, the target molecule may alternately be a non-protein, non-substrate molecule isolated from nature or made synthetically which may form a conjugate with CBD by means of covalent linkage subsequent to synthesis or by non-covalent linkage (such as affinity binding). A target molecule also refers to a molecule which may bind to a protein complex formed between the affinity tag and a protein where the affinity tag binds to a substrate. The molecule may be any of: an organic molecule or an inorganic molecule including a co-factor, ligand, protein, carbohydrate, lipid, synthetic molecule, ion, where the inorganic molecule further includes fluorophors and dyes or mixtures of any of the above.

"Substrate" refers to any molecule to which CBD will bind. This preferably includes chitin which is an insoluble $\beta$-1,4-linked homopolymer of N-acetyl-D-glucosamine, P. Jolles et al. Chitin and chitinases, Birkhäuser Verlag (1999), Basel., but may also include chitin analogues and derivatives that are naturally occurring or prepared in part or wholly by chemical synthesis. The substrate may be formed into beads, colloids, columns, films, sponges, filters, coating or other suitable surfaces for use in binding an affinity tag for purposes that include isolation or purification of a target molecule or analysis of the presence or amount of a target molecule in a diagnostic test format or for binding a marker as an indicator of a chemical reaction or other use.

"Modified CBD" refers to any change to a CBD that results in its binding to substrate being altered under select conditions where such alteration in binding would not occur in unmodified CBD.

"Selected condition(s)" refers to any condition which when applied to a conjugate of a target molecule and CBD bound to substrate via the CBD, causes reversal of binding. The selected condition is preferably required to be of the type that does not degrade the target molecule.

"Host cells" refers to cells that express target molecules, CBD and/or fusion proteins and include any known expression system in prokaryotes or eukaryotes including bacterial host cells, yeast, invertebrate, fish and mammalian cells including human cells.

Desirable Features of a Modified Cbd

Desirable features of a modified CBD may include any or all of the following:

(a) a size or other characteristics of the modified CBD should preferably not interfere with the function of the target protein to which it is associated. An advantage of non-interference is that cleavage of the CBD from the protein is not required to obtain purified active target protein. Indeed, where the size of the affinity tag is less then about 30 kb or less than 20 kd, interference with functionality of the target protein may be minimized or avoided. Examples VII-IX show that CBD (about 6 Kd) does not interfere with the function of a target recombinant protein EK-CBD. In those circumstances where the target protein is very small, a DNA sequence encoding a linking peptide sequence may be inserted between DNA for the affinity tag and the target peptide. The resultant fusion protein may be cleaved by a proteolytic agent to liberate the target protein after purification has been completed;

(b) an ability of the modified CBD to bind tightly to both a substrate and the target protein under one set of conditions and under a separate set of conditions, to maintain an association with the target protein while being eluted from the substrate. Example V shows how the binding of modified CBD to substrate can be made energetically less favorable under selected conditions by introducing mutations into the protein;

(c) an ability to recognize a substrate that is readily available in nature or capable of cost effective manufacture and may be formed into any of a variety of formats according to the desired use such as beads or columns for purification of a target molecules. FIG. 5A shows results of a one step chitin column purification of hGM-CSF-CBD and Her-2(KD)-CBD (FIGS. 5B and 5C);

(d) Absence of properties that cause degradation of the substrate by the modified CBD or target protein under the set of conditions in which the substrate is used to separate the target protein from a mixture. For example, the CBD lacks hydrolytic activity associated with chitinase where chitinase digests chitin.

Identifying a Suitable Modification of the Chitin Binding Domain by Targeted Mutation of the DNA Sequence Encoding the CBD Mutations in DNA which result in an altered amino acid sequence may be random or may be targeted to a specific amino acid or amino acids. One criteria for selecting an amino acid target is the location of the amino acid in the protein as determined by crystallographic data. For example, a targeted amino acid may be located on the surface of the CBD or within the binding cleft.

Figure 2A:
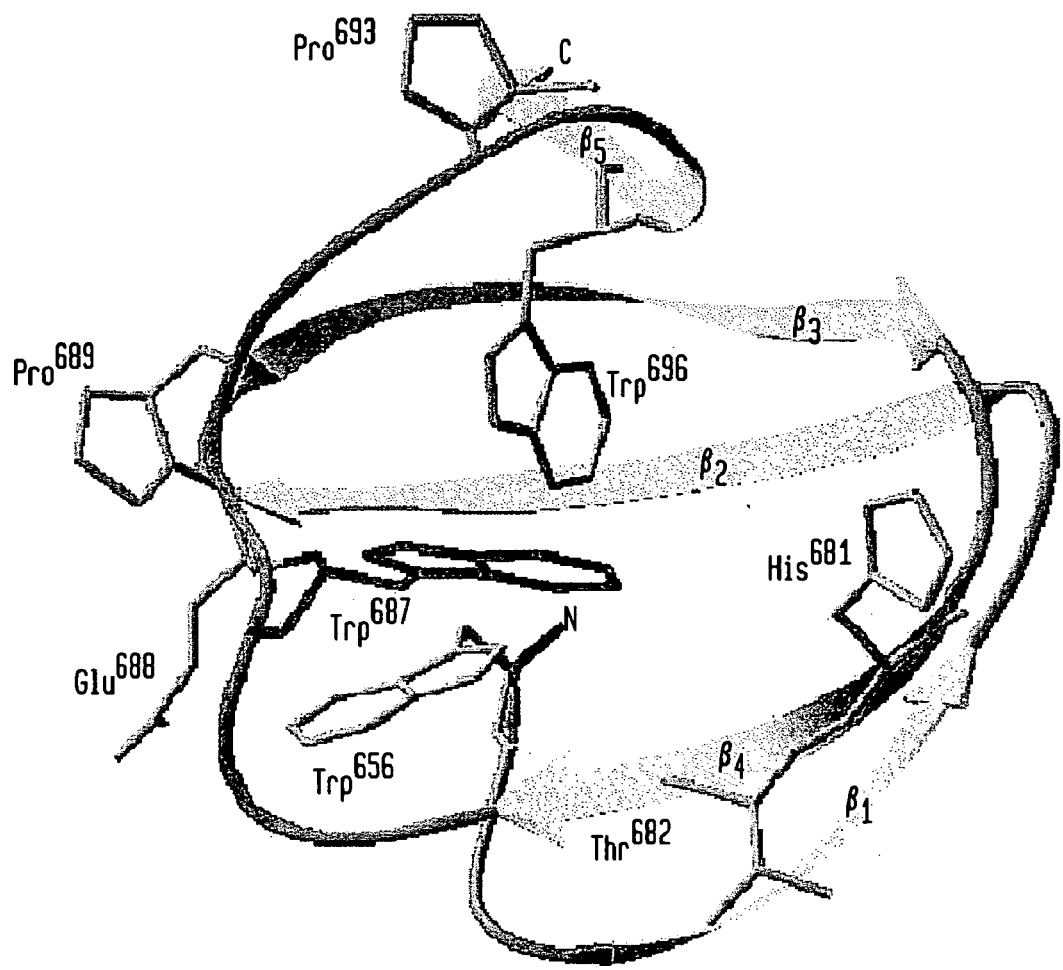
FIG. 2A. Drawing of the wild-type CBD of *Bacillus circulans* chitinase A1.
Figure 2B:
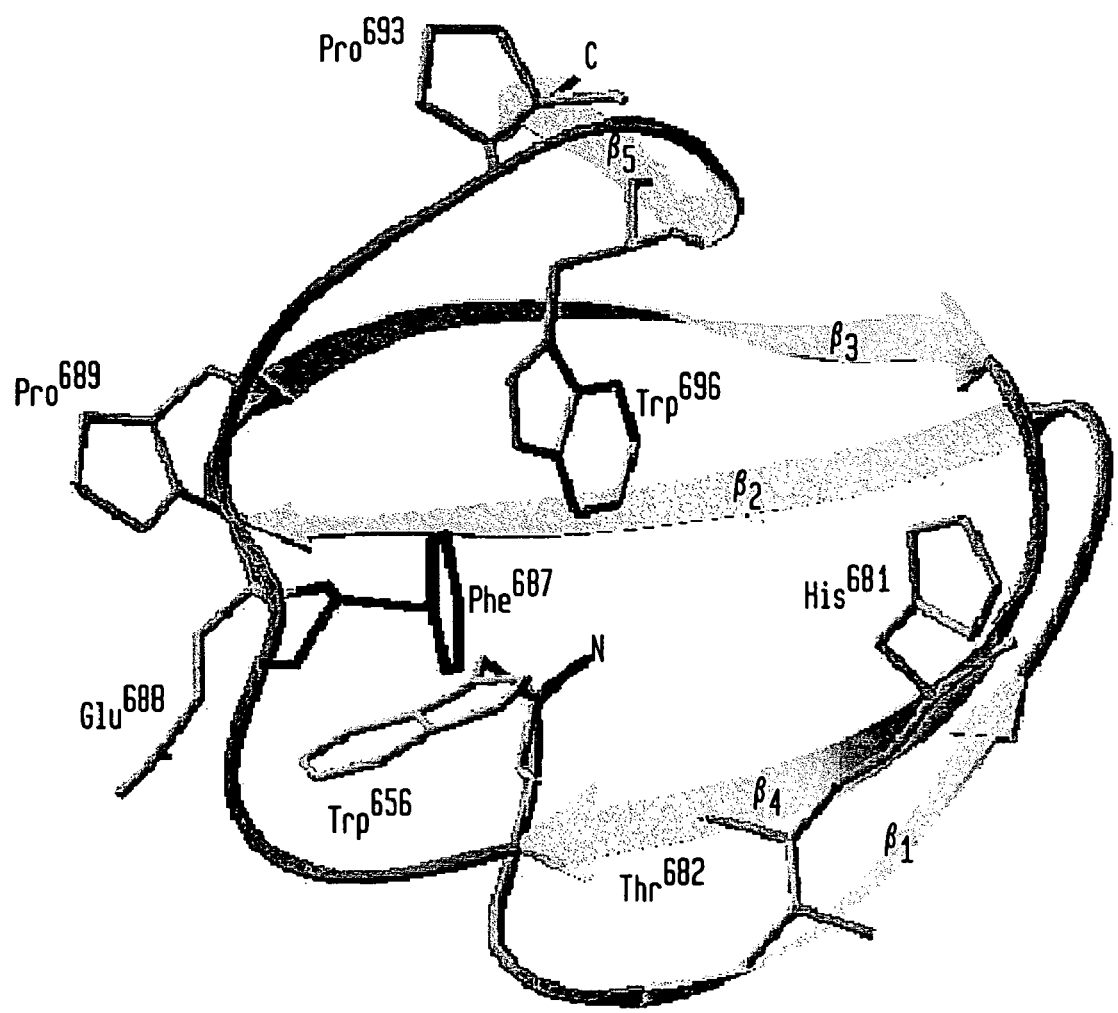
FIG. 2B. Drawing of the CBD harboring the W687F mutation. β-strands are shown as curved arrows in yellow. Secondary structure elements, N and C termini, and the mutated residues are labeled. Red color represents specifically the residue in position 687. The sequence of *Bacillus circulans* chitinase A1 was obtained from NCBI structures database and figures were obtained using Swiss-Pdb Viewer version 3.7b1.

In one embodiment of the invention, targeted mutagenesis results in changes to one or more amino acids in the 45 residues CBD selected according to the tertiary structure of the protein. As shown in FIG. 2, CBD has a compact and globular structure containing two antiparallel β-sheets and a core region formed by hydrophobic and aromatic residues. Several residues that may be important for the hydrophobic interaction with chitin may have one or more of the following properties: (i) they are well conserved among different bacterial chitinases; (ii) they exist on the surface of the molecule or in the hydrophobic core, and (iii) they are hydrophobic or aromatic amino acids with the potential to form hydrophobic interactions with chitin. For example, $Trp^{687}$, $Pro^{689}$ and $Pro^{693}$, are highly conserved among different bacterial chitinases and exist on the surface of the molecule with the potential to form hydrophobic interactions with chitin.

Using methods of targeted mutagenesis, such as described in Example I, any desired amino acid can be altered and the effect on binding of CBD to chitin measured under selected conditions. While the method of targeted mutagenesis using mutagenesis linkers is effective, there are many alternative approaches known to one of ordinary skill in the art for targeted mutagenesis which may alternatively be used to modify CBD. In Example I, mutations of amino acids at positions 681, 682 and 687 in the protein are described. However, the method of Example I could also be applied to mutating any other amino acid in the CBD. Once an altered CBD has been formed, it may be assayed according to Example II in order to determine whether the CBD is capable of reversible binding to its substrate.

In Example I, a mutant CBD with an altered amino acid at position 687 was found to be capable of reversible binding to chitin when the native Tryptophan which is a hydrophobic residue within the binding cleft of CBD was replaced with phenylalanine. This finding however does not preclude other amino acid substitutions at this location being effective although substitution with alanine, tyrosine or threonine, appeared to completely abolish CBD binding to chitin (FIG. 3). Nor does this finding preclude amino acid substitution at other locations in the protein. While not wishing to be bound by theory, it appears from the 3D structure of the CBD, that Trp687 lies in the binding surface formed between the two β-sheets and interacts directly with the chitin chain through hydrophobic interactions (FIG. 2) presumably involving aromatic ring polarization. Hence, while mutation of $Trp^{687}$ to phenylalanine still permitted binding at 2 M NaCl where the benzene ring of phenylalanine residue substituted for the indole ring of tryptophan, affinity of binding of CBD to chitin became altered so as to be responsive to altered ionic strength. In contrast, replacement of $Trp^{687}$ with tyrosine abolished binding to the chitin substrate probably due to the presence of a hydroxy-group on the phenyl ring that may interfere with the general hydrophobicity of the region.

Figure 3A:
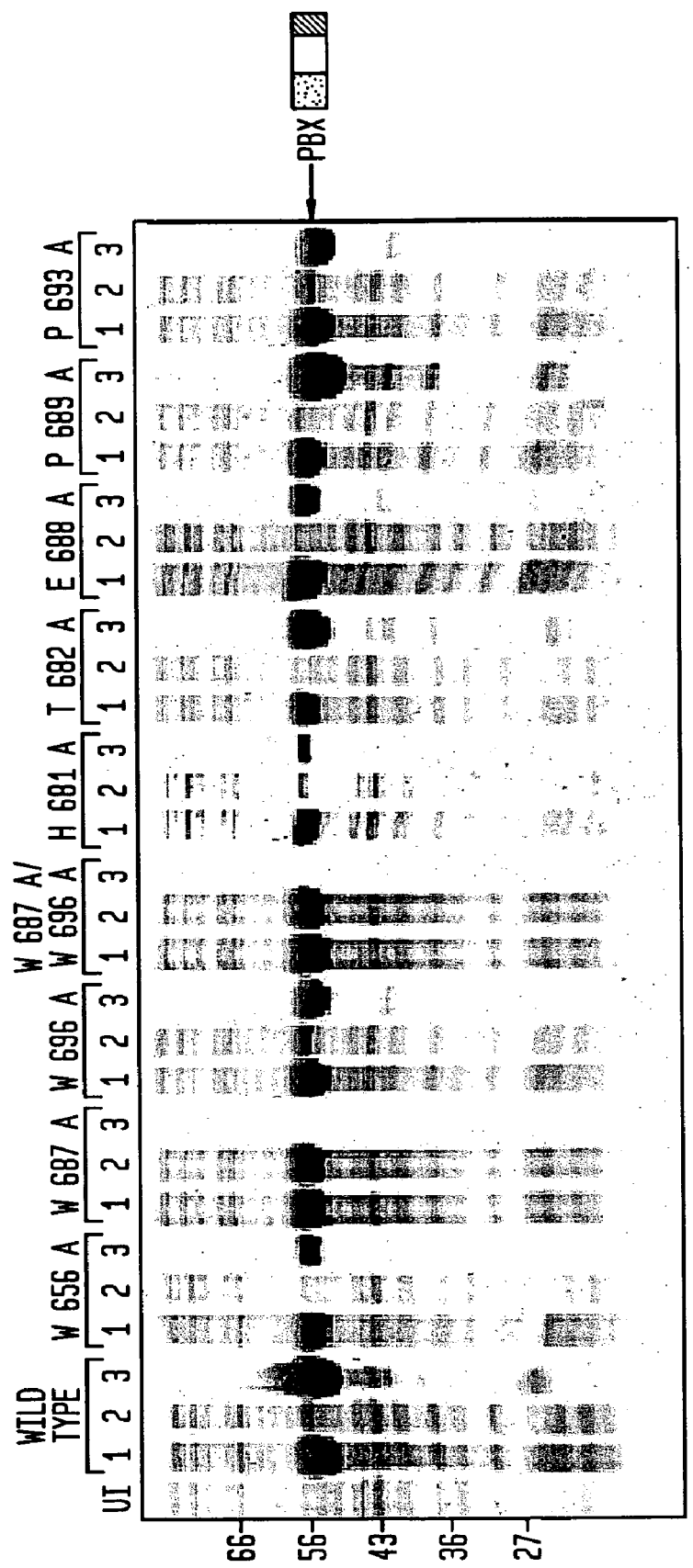
FIG. 3A. A chitin binding assay for each PXB protein carrying an alanine substitution was carried out in Tris-buffer (pH 8) containing 50 mM NaCl.
Figure 3B:
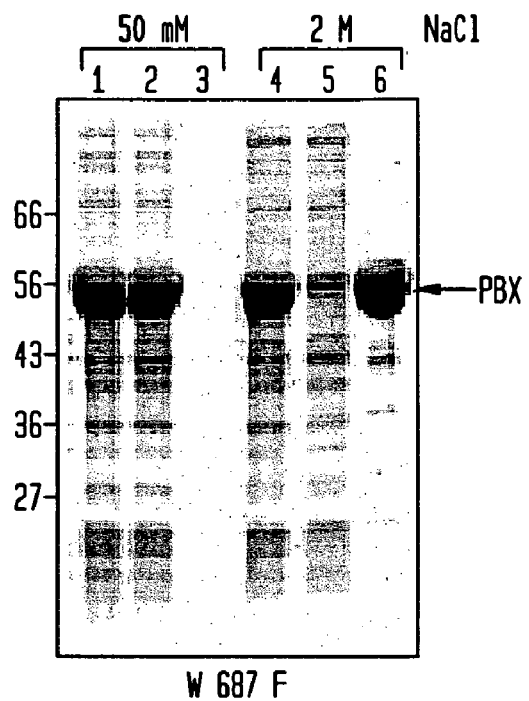
FIG. 3B. A chitin binding assays were performed in buffer containing either 50 mM NaCl (lanes 1–3) or 2 M NaCl (lanes 4–6) for the PXB mutant proteins carrying W687F.
Figure 3C:
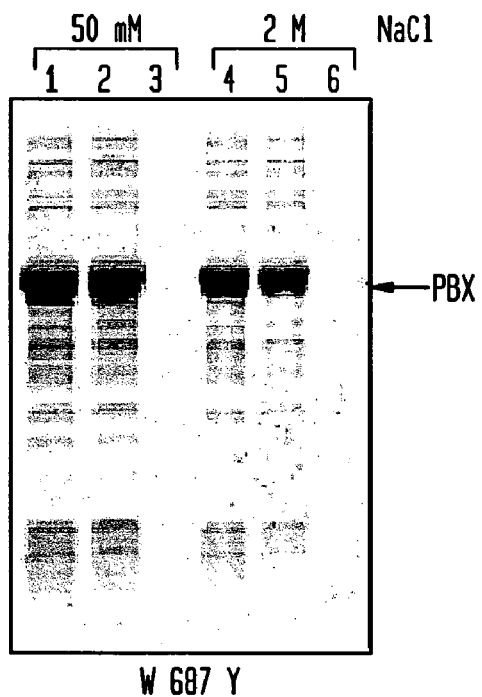
FIG. 3C. A chitin binding assay for W687Y in different NaCl conditions (50 mM NaCl in lanes 1–3 and 2M NaCl in lanes 4–6).
Figure 3D:
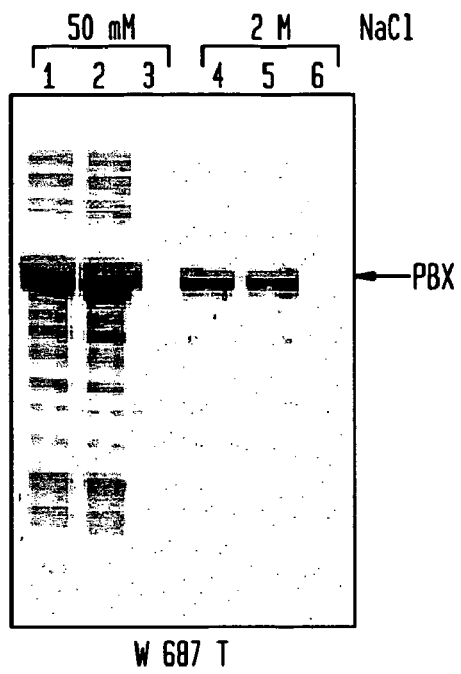
FIG. 3D. A chitin binding assay for W687T in different NaCl conditions (50 mM NaCl in lanes 1–3 and 2M NaCl in lanes 4–6).
Figure 3E:
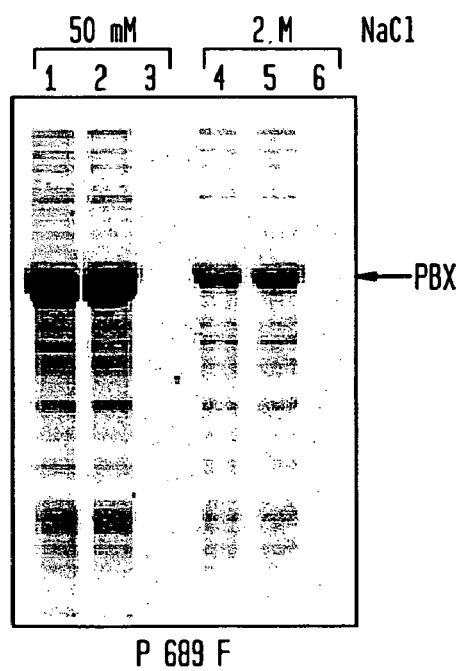
FIG. 3E. A chitin binding assay for P689F in different NaCl conditions (50 mM NaCl in lanes 1–3 and 2M NaCl in lanes 4–6).

Interestingly, mutation of Pro689 to phenylalanine in the CBD abolished binding to chitin while mutation to alanine showed no effect (FIGS. 3A and 3E). Pro689 is positioned in the loop between $β_4$ and $β_5$ in close proximity of Trp687. Due to the cyclic and rigid nature of its pyrolidine side group, introduction of phenylalanine in this position probably disturbs the positioning of Trp687 in the structure. Our results also indicate that single amino acid substitutions of Trp656 or Trp696 have no substantial effect on the chitin binding activity.

While hydrophobic amino acids have been initially targeted by mutagenesis, the findings do not preclude the possibility that non-hydrophobic amino acids in the CBD may be modified to provide reversible binding of CBD to chitin under select conditions. Moreover, while Example I describes a particular mutation in the CBD of *Bacillus circulans* chitinase A1, it is expected, based on evolution of CBD as a class, that modification to a targeted amino acid in a CBD from one source will cause a similar effect in CBDs in general.

Desirable modifications of CBD provide a high affinity of binding to chitin under one set of conditions with reversible binding under altered conditions. For example the altered conditions may be a shift in ionic strength of the elution buffer from one ionic strength to a greater or lesser ionic strength. For example, ionic strength may be altered by modifying the NaCl concentration in the buffer. For example, whereas modified CBD may bind irreversibly in a buffer having a salt concentration, in the range of 0.2 M–3M, the modified CBD may be eluted when the salt concentration is altered to 0.1–1M NaCl. While the above ranges overlap, it should be understood that it is intended that different concentrations of NaCl in buffer determine whether binding of CBD to substrate is reversible or non-reversible. Example III describes how in a buffer containing 2M NaCl, a modified CBD binds strongly to chitin while at a different salt concentration (50 mM NaCl), the affinity for CBD for substrate is reduced permitting elution of CBD from the substrate (Example III and IV). Alternatively, instead of changing salt conditions, pH may be changed to cause modified CBD to be reversibly bound to substrate. For example, CBD having a Try 687 modified to phenylalanine binds strongly to chitin at a pH in the range of 6 to 11. However, no or very poor binding of the CBD to chitin occurs at or below pH 5. Other selected conditions may include a change in temperature, change in detergent concentration or addition or removal of competitive binding molecules such as agonists or antagonists for example, oligopolysaccharide homologs of chitin or CBD analogs.

The formation of a conjugate of CBD with a target molecule may include either a covalent or non-covalent association between the component molecules. There are many methods known in the art for creating a conjugate. If the target molecule is a protein, the protein may be covalently linked to the CBD during recombinant synthesis in a host cell. Accordingly, the DNA sequence corresponding to CBD or target protein may be contained within a plasmid or chromosomal DNA in a host cell for expression of a fusion protein. In certain circumstances, the target protein may become covalently linked to the CBD after cleavage of an intein or alternatively a target protein may be linked to a CBD post translationally by protein ligation or by other means (U.S. Pat. No. 5,834,247; International Publication No. WO 00/47751 and WO 01/57183).

Genes coding for the various types of protein molecules including those described below may be obtained from a variety of prokaryotic or eukaryotic sources, such as plant or animal cells or bacteria cells. The genes can be isolated from the chromosomal material of these cells or from plasmids of prokaryotic cells by employing standard, well-known techniques. A variety of naturally occurring and synthetic plasmids having genes encoding many different protein molecules are now commercially available from a variety of sources. The desired DNA also can be produced from mRNA by using the enzyme reverse transcriptase.

Preparation of DNA fusion and expression vectors may be achieved as described in the art (U.S. Pat. No. 5,643,748) or as described in Example I or by other means known in the art. For example, the following protocol may be followed:

I. Preparation of Fusion Vector
A) The DNA encoding for the desired binding protein is purified.
B) The DNA is inserted into a cloning vector such as pBR322 and the mixture is used to transform an appropriate host such as E. coli.
C) The transformants are selected, such as with antibiotic selection or auxotrophic selection.
D) The plasmid DNA is prepared from the selected transformants.
E) The binding activity domain of the protein is determined and convenient restriction endonuclease sites are identified by mapping or created by standard genetic engineering methods.

II. Insertion of DNA Coding for the Protein Molecule into the Fusion Vector
A) The protein molecule gene is cloned by standard genetic engineering methods.
B) The protein molecule gene is characterized, e.g. by restriction mapping.
C) A DNA restriction fragment which encodes the protein molecule is prepared.
D) The protein molecule DNA fragment is inserted in the binding protein fusion vector so that an in-frame protein fusion is formed between the DNA fragment coding for the modified CBD and the DNA fragment coding for the protein molecule.
E) The vector containing this hybrid DNA molecule is introduced into an appropriate host.

III. Expression and Purification of the Hybrid Polypeptide
A) The host cell containing the fusion vector is cultured.
B) Expression of the fused gene is induced by conventional techniques.
C) A cell extract containing the expressed fused polypeptide is prepared.
D) The hybrid polypeptide is separated from other cell constituents using an affinity column having as a matrix a substance to which the modified CBD part of the hybrid polypeptide has a specific affinity.
E) The bound purified hybrid polypeptide can be recovered and/or utilized by the following methods:
(1) if the protein molecule's biological activity is maintained in its hybrid or fused configuration it may recovered from the column by eluting under selected conditions and used directly after elution in its hybrid form;
(2) the protein molecule may be separated from the modified CBD either before or after elution from the column by proteolytic or chemical cleavage; and
(3) the column may be used as a bioreactor with the fusion protein immobilized on the column, e.g. by contacting and reacting the bound fusion protein with a substrate which interacts with the biologically active portion of the protein molecule.

Linking Sequence

A DNA fragment coding for a predetermined peptide may be employed to link the DNA fragments coding for the binding protein and protein molecule. The predetermined peptide is preferably one which recognized and cleaved by a proteolytic agent such that it cuts the hybrid polypeptide at or near the protein molecule without interfering with the biological activity of the protein molecule. One such DNA fragment coding for a predetermined polypeptide is described in Nagai et al., Nature 309:810–812 (1984). This DNA fragment has the oligonucleotide sequence: ATC-GAGGGTAGG (SEQ ID NO:15) and codes for the polypeptide Ile-Glu-Gly-Arg (SEQ ID NO:16). This polypeptide is cleaved at the carboxy side of the arginine residue using blood coagulation Factor Xa. As noted above the linking sequence, in addition to providing a convenient cut site if such is required, may also serve as a polylinker, i.e. by providing multiple restriction sites to facilitate fusion of the DNA fragments coding for the target and binding proteins, and/or as a spacing means which separates the target and binding protein which, for example, allows access by the proteolytic agent to cleave the hybrid polypeptide. Other examples of linkers include GATGACGATGACAAG (SEQ ID NO:45) coding for Asp-Asp-Asp-Asp-Lys (SEQ ID NO:46) which is cleaved by enterokinase I and CCGGGT-GCGGCACACTCAC (SEQ ID NO:47) coding for Pro-Gly-Ala-Ala-His-Tyr (SEQ ID NO:48) which is cleaved by Genenase I (New England Biolabs 2002/2003 Catalog, page 163; Beverly, Mass.). Other linkers not generally cleaved by a protease include a polyasparagine linker which consists of 10 Asp amino acids and is encoded by AACAACAACAA-CAACAACAACAACAACAAC (SEQ ID NO:49) and a "kinker" linker from M13 gene 3 protein with a Gly-Gly-Ser-Gly sequence.

The formation of a conjugate of modified CBD with the target molecule provides special advantages in purifying target molecules on a large scale or small scale. In Examples, VI–IX, the target molecule was expressed in host cells as a fusion protein with modified CBD. The fusion protein whether present in the production media or associated with the host cells which may be disrupted after harvesting, becomes immobilized by binding to substrate. After removal of the unbound material, the substrate to which the fusion protein is bound is subjected to non-denaturing conditions such as a particular ionic concentration or pH causing the fusion protein to be released into a selected buffer. The insoluble substrate can then be removed by precipitation, filtration or other standard techniques for removal of particles from a solution. Where the CBD does not interfere with the function of the target protein, cleavage of the CBD from the target protein is not required.

The above approach finds application in the purification of secreted proteins in microbial fermentation. Whereas purification of secreted proteins have the advantage of avoiding breaking the host cells prior to recovery, the desired secreted proteins may be present in large volumes of growth media. Handling large volumes of growth media presents a set of problems for which a solution would be desirable. For example, the yeast Kluyveromyces lactis is an important organism for industrial scale production of proteins. For over a decade, K. lactis has been used for heterologous protein production in the food industry due to its ability to grow to high cell density and secrete large amounts of recombinant protein. A drawback to the protein secretion method is that typically large volumes of culture medium must be processed to obtain highly purified recombinant protein. To demonstrate one approach to this, we have shown how secreted bovine enterokinase-CBD fusion protein can be purified from batch harvests using a mutant version of the *Bacillus circulans* chitinase A1 CBD as an affinity tag (Examples VII–IX).

The ability to alter the chitin binding domain from chitinase, so as to make its binding to substrate reversible significantly enhances the utility of this protein for purification of target molecules from different environments including from simple or complex mixtures of molecules in small or large liquid volumes.

The present invention is further illustrated by the following Examples. These Examples are provided to aid in the understanding of the invention and are not construed as a limitation thereof.

The references cited above and below are herein incorporated by reference.

EXAMPLE I

Plasmid Construction

The vector pPXB expresses a tripartite fusion protein consisting of the *Dirofilaria immitis* paramyosin ΔSal/I fragment (Steel et al., *J. Immunol.*, 145:3917–3923 (1990)) followed by the Mxe GyrA intein of *Mycobacterium xenopi* (Mxe intein) and the wild type CBD from *Bacillus circulans* WL-12 fused to the C-terminus of the intein (Evans et al., *Biopolymers* 51:333–342 (1999a)). The sequence encoding human granulocyte-macrophage colony-stimulating factor (hGM-CSF) (Cantrell et al., *Proc. Natl. Acad. Sci. USA*, 82:6250–6254 (1985); Mingsheng et al., *J. Biotechnol.* 1995:157–162 (1995)) was amplified by polymerase chain reaction (PCR) using hGM-CSF cDNA (ATCC-39754) as template and the primers: 5'-CTC GAGCATATGGCAC-CCGCCCGCTCGC-3' (SEQ ID NO:17) and 5'-CGTGGT-TGCTCTTCCGCACTCCTGGACTGGCTCCCAGCAG-3' (SEQ ID NO:18). The resulting product was cloned into pTWIN1 vector (Evans et al., *J. Biol. Chem.*, 274: 18359–18363 (1999b)) using NdeI and SapI sites yielding pGM-CSF-XB. Expression of this construct produces hGM-CSF fused to the Mxe intein-CBD. A HindIII site was introduced into the CBD wild type sequence by silent base substitution. To do this, the intein-CBD coding region was amplified by PCR using Vent® DNA polymerase (New England Biolabs, Inc.; Beverly, Mass.) and the following primers 5'-AGATGCACTAGTTGCCCTAC-3' (SEQ ID NO:19) and 5'-TGTACGCTGCAGTTACAAGCTTGT-GTGGGGCTGCAAACATTAT-3' (SEQ ID NO:20). The resulting fragment was cloned in-frame in pPXB and pGM-CSF-XB vectors using the SpeI and PstI sites thereby replacing the original CBD sequence by a CBD with a 16 amino acid deletion of its C-terminus. The following oligonucleotides and their appropriate complement were used to introduce the missing C-terminal residues into the HindIII and PstI sites in both vectors: W687F, 5'-AGCTTGGCAG-GATTT GAACCATCCAACGTTCCTGCCTTGTGGCA GCTTCAATAACTGCA-3' (SEQ ID NO:21); W687A/W696A, 5'-AGCTTGGCAGGAGCCGAA CCATC-CAACGTTCCTGCCTTGGCCCAGCT-TCAATAACTGCA-3' (SEQ ID NO:22); W687F/W696F, 5'-AGCTTGGCAGGATTTGAACCACCA ACGTTCCT-GCCTTGTTTCAGCTTCAATAACTGCA-3' (SEQ ID NO: 23); W687T, 5'-AGCTTG GCAGGAACCGAACCATC-CAACGTT CTGCCTTGTGGCAGCTTCAATA ACT-GCA-3' (SEQ ID NO:24); W687Y, 5'-AGCTTGGCAG-GATATGAACCATCCAACGTTCCTGCCT TGTGGCAG CTTCAATAACTGCA-3' (SEQ ID NO:25); P689A, 5'-AG CTTG G CAG GATG GGAAG CCTCCAACGTTCCTGC-CTTGTGGCAGCTTC AATAACTGCA-3' (SEQ ID NO:26); P689F, 5'-AGCTTGGCA GGATGGGAAT-TllCCAACGTTCCTGCCTTGTGGCAGCT-TCAATAACTGCA -3' (SEQ ID NO:27); P693A, 5'-AGCT-TGGCAGGATGGGAACCAT CCAACGTTGCCGCCTTGTGGCAGCT-TCAATAACTGCA-3' (SEQ ID NO:28); P693F, 5'-AGCT-TGGCAGGATGGGAACCATCCAACGTTGC CTTGTG-GCAGCTTCAATAACTGCA-3' (SEQ ID NO:29); W696F, 5'-AGCTTGGC AGGATGGGAACCATCCAACGTTCCT-GCCTTGTTTCAGCT TCAATAACTGCA-3' (SEQ ID NO:30). The mutagenesis linkers were formed by annealing appropriate complementary oligonucleotides. Other CBD mutations were introduced into pGM-CSF-XB vector by linker replacement using the AgeI and MfeI sites and the following oligonucleotides and their appropriate complement: W656A, 5'-CCGGTCTGAACTCAGGC CTCAC-GACAAATCCTGGTGTATCCGCTGCCCAG-GTCAACACAG CTTATACTGCGGGAC-3' (SEQ ID NO:31); W656F, 5'-CCGGTCT GAACTCAGGCCTCAC-GACAAATCCTGGTGTATCCGCTTTTCAGGTC AACA-CAGCTTATACTGCGGGAC-3' (SEQ ID NO:32). Mutations in position 681 and 682 into MfeI and HindIII sites were achieved using the following oligonucleotides and their complement: H681A, 5'-AATTGGTCACATATAACG-GCAAGACGTAT AAATGTTTGCAGCCCGCCACA-3' (SEQ ID NO:33); H681F, 5'-AA TTGGTCACATATAACG-GCAAGACGTATAAATGTTTGCAGCCCTTTACA-3' (SEQ ID NO:34); T682A, 5'-AATTGGTCACATATAACG-GCAAGA CGTATAAATGTTTGCAGCCCCACGCA-3' (SEQ ID NO:35). pGM-CSF-XB constructs containing mutations were transferred into PPXB using SpeI and HindIII sites. pGM-CSF-CBD vector was constructed by replacing the Mxe GyrA intein coding region in PGM-CSF-XB plasmid carrying the W687F mutation by a short linker using the SpeI and AgeI sites and the following oligonucleotides and their appropriate complements: 5'-CTA GTGC-CCGGGCCAA-3' (SEQ ID NO:36). pCBD was constructed by replacement of the sequence coding for the paramyosin and the Mxe GyrA intein in pPXB carrying the W687F mutation with a polylinker using the following oligonucleotide and its appropriate complement: 5'-AGCTTGGCAG-GATATGAACCA TCCAACGTTCCTGCCTTGTG-GCAGCTTCAATAACTGCA-3' (SEQ ID NO:37). The polylinker region permits cloning of a gene of interest in-frame to the mutated CBD. The sequence encoding the kinase domain of Her-2 [Her-2(KD)] (Yamamoto et al., *Nature* 319:230–234 (1986)); Doherty et al., *Proc. Natl. Acad. Sci. USA* 96:10869–10874 (1999)) was amplified by PCR using Human Heart Marathon Ready cDNA (Clontech; Palo Alto, Calif.) and the following primers: 5'-GGCTCT-TCCATGCGGAGACTG CTGCAGGAAACGGAG-3' (SEQ ID NO:38) and 5'-GGCTCTTC CGCCGCCCT-GCTGGGGTACCAGATACTCCTC-3' (SEQ ID NO:39). The resulting product was cloned into pCBD using the SapI site yielding pHer-2(KD)-CBD vector. pHer-2(KD)-CBD expresses a two-part fusion protein consisting of the cytoplasmic kinase domain of the human Her-2 protein [Her-2 (KD)] fused at its C-terminus to the CBD harboring the W687F mutation.

EXAMPLE II

In Vitro Chitin-Binding Assay

*Escherichia coli* strain ER2566 (New England Biolabs, Beverly, Mass.; Chong et al., Gene 192:271–281 (1997)), harboring PPXB or its mutant derivatives, was grown at 37° C. in 1 liter of LB medium containing 100 µg/ml of ampicillin to an $A_{600}$ of 0.5–0.7. The culture was induced with 0.3 mM isopropyl-β-D-thiogalactoside (IPTG) at 30° C. for 3 hours or at 16° C. overnight under the control of the T7 promoter (Studier et al., *Methods Enzymol.,* 185:60–89 (1990)). The proteins expressed from pPXB are referred to as PXB fusion proteins in our study. The binding assay was carried out by resuspension of the cell pellet in 20 mM Tris-HCl (pH 8) containing 2 M or 50 mM NaCl. Following sonication of the resuspended cell pellet, debris was removed by centrifugation at 4,000×g for 30 minutes. Clarified supernatants were loaded at 4° C. onto a column with a 3 ml bed volume of beads made of insoluble chitin (New England Biolabs, Beverly, Mass.) previously equilibrated in the same buffer as that used for resuspension. Equivalent amounts of load, flow—through, and a sample of chitin beads for each of the NaCl concentrations were analysed by electrophoresing a 12% Tris-glycine gel (Invitrogen, Carlsbad, Calif.) and staining with Coomassie Brilliant Blue for visualisation.

EXAMPLE III

Assay for Nacl-Dependent Chitin-Binding and Elution

Expression of the PXB (W687F) fusion protein was conducted as described above. Binding of the PXB (W687F) mutant protein to chitin was carried out in 20 mM Tris-HCl (pH 8) containing either 2, 1, 0.5 or 0.05 M NaCl. Appropriate buffer was used for resuspension of the cell pellet and wash of chitin resin after loading. For the elution assay, resuspension of cell pellet and sonication were performed using the 20 mM Tris-HCl (pH 8) buffer containing 2 M NaCl. After the centrifugation step of the cell extract, the supernatant was loaded onto a chitin column previously equilibrated with buffer containing 20 mM Tris-HCl (pH 8) and 2 M NaCl. The PXB protein was eluted with 20 mM Tris-HCl (pH 8) buffer containing either 1 M, 0.5 M, 0.1 M or 50 mM NaCl. Thirty 1-ml fractions were collected. NaCl concentration of the 50 mM NaCl-eluted fraction was shifted back to 2 M in order to test whether binding was a reversible phenomenon. Recombinant proteins for the NaCl-dependent chitin binding and elution assay were subjected to SDS-PAGE analysis on 12% Tris-glycine gel and the protein concentration was determined by Bradford assay (Bradford, *Anal. Biochem.,* 72:248–254 (1976)) (Biorad, Cambridge, Mass.).

EXAMPLE IV

Effect of CBD Mutations on Binding to Insoluble Chitin

In order to investigate the contribution of highly conserved residues of chitinase A1 CBD to chitin binding activity, single alanine substitutions were constructed in a 56 kDa fusion protein PXB possessing a C-terminal CBD as summarized in Table 1. The binding activities of the alanine replacement mutants were assayed by passage of the clarified induced cell extract over chitin resin in a buffer containing 50 mM NaCl. SDS-PAGE was used to examine the binding efficiency by comparing the load to the flow-through. In addition, a fraction of chitin resin was also subjected to SDS-PAGE analyses after extensive washing of the column. As shown in FIG. 3, all alanine mutant proteins, except the W687A and the W687A/W696A double mutants, bound efficiently to chitin resin as indicated by the absorption of most PXB by the chitin resin after passage over the column (lane 2) and the presence of PXB species in the chitin resin fraction following a wash step (lane 3). In contrast, the W687A and the W687A/W696A double substitutions abolished the chitin binding activity since the amount of PXB species was not significantly reduced in the cell extract after passage over the column and was not present in the chitin resin fraction (W687A and W687A/W696A, lanes 2 and 3). Furthermore, the same pattern of binding was obtained when binding assays were conducted with a 20 mM Tris-HCl buffer containing 2 M NaCl (data not shown). Therefore, the data suggested that W687 plays an important role in the interaction between CBD and chitin.

Based on structural modeling (FIG. 2), we reasoned that a conservative replacement by a hydrophobic and aromatic residue such as phenylalanine might compensate and mimic the role of W687. When the binding assay was performed in a buffer containing 50 mM NaCl, it appeared that the binding profile for the PXB (W687F) mutant protein (lanes 2 and 3, FIG. 3B) was similar to that of the alanine substitution mutant. The binding assay was further performed in a buffer containing 2 M NaCl to assess whether interaction of the mutant proteins to chitin could be affected by ionic strength since higher salt concentration might enhance hydrophobic interaction and therefore increase the binding efficiency of the CBD to chitin. Under high salt conditions, the PXB protein harboring the W687F mutation (lanes 5 and 6, FIG. 3B) was functionally active and bound chitin as indicated by a significant decrease of the PXB (W687F) species in the flow-through (lane 5) and its presence in the chitin resin fraction (lane 6). The results suggested that binding activity can be restored by the introduction of a phenylalanine residue at position 687 with a concomitant increase in NaCl concentration. On the other hand, replacement of W687 with tyrosine appeared to interfere with binding to chitin possibly due to an additional hydroxy group on the phenyl ring. The binding of the W687Y mutant was noticeably decreased in the reaction mixture containing either 50 mM or 2 M NaCl (FIG. 3C). The low affinity of this PXB species for chitin was evident since most of the mutant protein remained in the extract after passage over chitin resin at both 50 mM and 2 M NaCl concentration (lanes 2 and 5) and was absent in the sample of chitin beads (lanes 3 and 6). Furthermore, replacement of Trp687 by a threonine residue also resulted in a failure to bind chitin (FIG. 3D).

Mutation of other hydrophobic and aromatic residues, W656, H681, P693 and W696 to phenylalanine did not significantly affect the affinity to chitin in either 2 M or 50 mM NaCl (data not shown). However, introduction of a phenylalanine residue in place of Pro689 caused a substantial decrease in the binding efficiency (FIG. 3E) compared to the P689A mutation, resulting in an increase of the mutant protein in chitin flow-through (lane 2) and little protein on the chitin resin (lane 3). The W687F/W696F double mutant showed essentially the same binding efficiency as the W687F mutant, suggesting that there was no cumulative effect between those two residues. Finally, substitution of Glu688, a conserved charged residue on the surface, with alanine or glutamine did not significantly affect the binding to chitin at both low and high salt concentrations (FIG. 3A). Thus, these conserved residues do not appear to be essential for chitin binding.

TABLE 1

Characterization of chitin-binding domain mutants

| Mutants | Percentage of chitin binding in various NaCl concentration | |
|---|---|---|
| | 2 M | 0.05 M |
| WT | >90 | >90 |
| $W^{656}A$ | >90 | >90 |
| $H^{681}A$ | >90 | >90 |
| $T^{682}A$ | >90 | >90 |
| $W^{687}A$ | <10 | <10 |
| $E^{688}A$ | >90 | >90 |
| $P^{689}A$ | >80 | >90 |
| $P^{693}A$ | >80 | >80 |
| $W^{696}A$ | >80 | >90 |
| $W^{687}A/W^{696}A$ | <10 | <10 |
| $W^{656}F$ | >90 | >90 |
| $H^{681}F$ | >90 | >90 |
| $W^{687}F$ | >90 | <10 |
| $W^{687}T$ | <10 | <10 |
| $W^{687}Y$ | <10 | <10 |
| $P^{689}F$ | <10 | <10 |
| $P^{693}F$ | >90 | >90 |
| $W^{696}F$ | >60 | >90 |
| $W^{687}F/W^{696}F$ | >80 | <10 |
| $E^{688}Q$ | >90 | >90 |

EXAMPLE V

Effect of Ionic Strength on Chitin-Binding and Elution

To further analyze the effect of ionic strength on the affinity to chitin, binding of the W687F mutant was assessed in buffer containing 2 M, 1 M, 0.5 M or 50 mM NaCl. As shown in FIG. 4A, the binding efficiency of the W687F mutant correlated with the ionic strength of the buffer. Increasing the NaCl concentration from 50 mM to 0.5 M or 1 M resulted in partial binding of PXB (W687F) protein, as indicated by the presence of PXB in a sample of chitin resin after loading and washing (0.5 M and 1 M, lane 3). In contrast, binding at 2 M NaCl concentration permitted efficient binding to chitin indicated by the presence of only a trace amount of the PXB species in the chitin flow-through (2 M, lane 2) and the presence of PXB in the chitin resin fraction (2 M, lane 3).

The observation that the W687F mutant protein was incapable of binding chitin in 50 mM NaCl implied that the elution of the bound CBD fusion protein might be conducted by lowering NaCl concentration. Indeed, after loading and washing at 2 M NaCl, PXB proteins were efficiently eluted in buffer containing 50 mM or no NaCl (lanes 4 and 5, FIG. 4A). We further examined whether the chitin binding activity of the W687F mutant is reversible by adjusting the NaCl concentration of the eluted protein from 50 mM to 2 M NaCl. PXB fusion protein bound to chitin efficiently since it was completely depleted in the chitin flow-through and was present in the chitin resin fraction (lanes 6 and 7, FIG. 4A). Furthermore, different ionic strengths were used for elution after absorption and wash in the buffer containing 2 M NaCl (FIG. 4B). In the control experiment, the PXB protein possessing the wild type CBD exhibited a very weak elution with buffer containing 50 mM NaCl. The assay of the W687F mutant showed that 50 mM NaCl was sufficient for release of the mutant protein from chitin. Although the protein was partially eluted in buffers containing 0.1 to 1 M NaCl less protein was released from chitin beads in correlation to the increase in ionic strength.

EXAMPLE VI

One-Step Affinity Purification of CBD Fusion

Proteins

Modification of CBD for example using the CBD (W687F) mutant resulted in an elutable affinity tag for single column purification of recombinant proteins. A protein fused to the mutated CBD could be purified by chitin resin in a high salt buffer (e.g. 2 M NaCl) and released by simply shifting the NaCl concentration in the elution buffer to 50 mM NaCl (FIG. 5A). This was further demonstrated using human granulocyte-macrophage colony stimulating factor (hGM-CSF) and the kinase domain of Her-2 [Her-2 (KD)] both fused at their C-terminus to the mutated chitin binding domain (FIG. 5B and FIG. 5C).

Expression of PGM-CSF-CBD or pHer-2(KD)-CBD in E. coli ER2566 cells was carried out at 30° C. for 3 hours in the presence of 0.3 mM IPTG when cell-density reached an $A_{600}$ of 0.5–0.7. Induced cells were collected by centrifugation and resuspended in 20 mM Tris-HCl (pH 8) containing 0.5 M NaCl. Both fusion proteins were found in inclusion bodies which were isolated by breaking cells by sonication followed by centrifugation at 15,000×g for 30 min. The proteins were then solubilized in 20 mM Tris-HCl (pH 8) containing 0.5 M NaCl, 7 M Guanidine-HCl and 10 mM DTT and insoluble components were removed by centrifugation at 15,000×g for 30 min. To renature insoluble fusion proteins, the supernatant was dialyzed successively at 4° C. against 20 mM Tris-HCl (pH 8) and 0.5 M NaCl containing: 8 M urea, 10 mM DTT; 6 M urea, 1 mM DTT; 4 M urea, 1 mM DTT; 2 M urea, 0.1 mM oxidized glutathione, 1 mM reduced glutathione. Renatured fusion proteins were dialyzed twice against 20 mM Tris-HCl, 0.5 M NaCl containing 0.1 mM oxidized glutathione, 1 mM reduced glutathione, and no urea. Insoluble components were removed by centrifugation at 15,000×g for 30 min and the final NaCl concentration was increased to 2 M. Binding was performed by loading the supernatant onto a 25 ml chitin resin equilibrated in 20 mM Tris-HCl (pH 8) containing 2 M NaCl. The column was washed with 30 column volumes of the same buffer and then flushed with the elution buffer containing 20 mM Tris-HCl (pH 8) and 50 mM NaCl. Proteins were analyzed with a 12% Tris-glycine gel and the concentration was determined by Bradford assay.

Both hGM-CSF-CBD and Her-2(KD)-CBD fusion proteins were expressed in E. coli strain ER 2566 as inclusion bodies and consequently absent in the clarified cell extract after centrifugation (FIG. 5, lane 3). After solubilization and renaturation steps, these fusion proteins remained soluble and were applied to chitin resin at 2 M NaCl. Analysis of chitin beads after loading and washing at 2 M confirmed that both recombinant proteins were absorbed onto chitin (lane 6). Binding was approximately 80% for hGM-CSF-CBD and essentially 100% for Her-2(KD)-CBD (lane 5). Analysis by SDS-PAGE showed a prominent and single band corresponding to the expected hGM-CSF-CBD and Her-2(KD)-CBD fusion protein when a buffer containing 50 mM NaCl was used to elute the bound fusion proteins (lane 7). The obtained yields were 12.7 mg fusion protein per 1 liter cell culture for hGM-CSF-CBD and 4.5 mg per liter for Her-2 (KD)-CBD.

EXAMPLE VII

Method for Secreting and Purifying Bovine Enterokinase From Kluyveromyces Lactis A DNA fragment encoding bovine enterokinase with a c-terminal mutant CBD fusion [EK-CBD(W275F)] was created by PCR amplification from a template consisting of a *K. lactis* expression vector containing enterokinase with a wild-type CBD fusion (pEK-CBD). The forward primer for amplification was 5'-CCGCTCGAGAAAAGAATTGTTG-GTGGTTCTGATTCTAGA-3' (SEQ ID NO:40) and the reverse primer 5'-ATAAGAATGCGGC CG CTCAT-TGAAG CTG CCACAAGGCAG GAACGTTGGATGGT-TCAAATCCT GCC-3' (SEQ ID NO:41). The reverse primer directs incorporation of a 2 bp mutation into the CBD region (bold/underline) thus converting it from wild-type to the W275F mutant form. To facilitate subcloning, forward and reverse primers also contained sequences for XhoI and NotI restrictions sites (single underline), respectively. PCR conditions consisted of Vent® DNA polymerase in 20 mM Tris-HCl (pH 8.8 at 25° C.) containing 10 mM KCl, 10 mM $(NH_4)_2SO_4$, 4 mM $MgSO_4$, and 0.1% Triton X-100. The reaction mixture (50 μl total volume) contained 1 μM of each primer, 200 μM dNTPs and 60 ng of pEK-CBD. The reaction was initiated using a "hot start" procedure consisting of incubation at 95° C. for 5 min then 80° C. for 1 min at which time 2 U Vent® DNA polymerase was added. Thermocycling was performed for 30 cycles of successive incubations at 95° C. for 30 s, 59° C. for 30 s and 72° C. for 1 min, followed by a final 72° C. incubation for 5 min. The PCR product was purified via the QIAQuick PCR Isolation Kit (Qiagen Inc., Studio City, Calif.).

All of the purified DNA was cleaved with NotI and XhoI as follows: purified PCR product (30μl) was mixed with 5 μl of 10×NEBuffer 3 (500 mM Tris-HCl, 100 mM $MgCl_2$, 1 M NaCl, 10 mM dithiothreitol), 1 μl BSA (10 mg/ml), 1 μl each of both NotI (20 U) and XhoI (20 U), and distilled water (12 μl), followed by incubation at 37° C. for 2 h. The reaction was terminated by heating to 65° C. for 10 min, and the cleaved DNA purified via the QIAQuick PCR Isolation Kit. The cleaved DNA was ligated into NotI-XhoI cleaved pGBN2 (an integration vector for *K. lactis* expression) as follows: 500 ng of NotI-XhoI cleaved PCR product (3 μl) was mixed with 500 ng of NotI-XhoI cleaved pGBN2 (3 μl), 2 μl of 10× Ligation Buffer (500 mM Tris pH 7.5, 100 mM $MgCl_2$, 100 mM dithiothreitol, 5 mM ATP), 11 μl distilled water, and 1 μl (1 U) of ligase, and incubated for 15 h at 4° C. The ligation was desalted by microdialysis on a 0.025 μm membrane (Millipore Inc., Bedford, Mass.) at RT for 30 min. Ligated DNA (10 μl) was electroporated into *E. coli* ER2268. *E. coli* was prepared for electroporation by growing 1 L of cells to an optical density of 0.5 in L-broth. The cells were chilled on ice for 15 to 30 min then pelleted at 4° C. by centrifugation at 4000 rpm for 10 min. The cell pellet was washed twice in sterile cold water and once in cold 10% glycerol, then resuspended in 2 ml 10% glycerol to a final cell concentration of ~3×10$^{10}$ cells per ml. Cells were stored in 70 μl aliquots at −70° C. until needed. To electroporate DNA into *E. coli*, frozen cells were thawed on ice and mixed with 10 μl of the microdialyzed ligation. The mixture was placed into a cold 0.2 cm electroporation cuvette and a pulse of electricity (2.5 KV, 25 pF and 200 Ohm) was applied to the cell mixture. The *E. coli* was immediately diluted with 1 ml L-broth, grown at 37° C. for 30 min, and plated on L-agar plates containing 100 μg/ml ampicillin. After overnight incubation, screening for colonies carrying plasmids that successfully ligated the PCR product (described above) was performed by growing 10 ml cultures (L-broth with 100 ug/ml ampicillin) from 10 single transformants. Plasmid DNA was isolated from each culture using the QIAprep Spin Miniprep Kit from Qiagen Inc. (Studio City, Calif.). Clones with inserts were identified by digesting miniprep DNA as follows: 5 μl (1 μg) plasmid DNA was mixed with 5 μl of 10×NEBuffer 3 (500 mM Tris-HCl, 100 mM $MgCl_2$, 1 M NaCl, 10 mM dithiothreitol), 1 μl BSA (10 mg/ml), 1 μl each of both NotI (20 U) and XhoI (20 U), and 38 μl deionized water, followed by incubation at 37° C. for 2 h. Digested DNAs were subjected to electrophoresis through a 1% agarose gel in Tris-Acetate-EDTA (TAE) buffer. Clones containing a 903 bp insert were subjected to automated sequencing using pGBN2-specific primers 5'-TCCGAG CTCAAAACAATGAGATTTCCTTCAAT TTTTACT-3' (forward) (SEQ ID NO:42) and 5'-GCATGTATACAT CAG-TATCTC-3' (reverse) (SEQ ID NO:43) to confirm proper incorporation of the 2 bp mutation into the CBD region.

EXAMPLE VIII

Secreted Expression of EK-CBD(W275F) IN *K. LACTIS*

To integrate DNA encoding EK-CBD(W275F) into the chromosome of *K. lactis* for expression, clones of DNA encoding EK-CBD(W 275F) in pGBN2 were first linearized by digestion with SacII as follows: 15 μl (3 μg) plasmid DNA, 5 μl 10×NEBuffer 4 (200 mM Tris-acetate, 100 mM magnesium acetate, 500 mM potassium acetate, 10 mM dithiothreitol), 2 μl (40 U) SacII, and 28 μl deionized water were mixed and incubated at 37° C. for 4h. Digested vector was purified via the QIAQuick PCR Isolation Kit (Qiagen Inc., Studio City, Calif.) and eluted in 30 μl deionized water. Linearized DNA (10 μl) was introduced into *K. lactis* GG799 and integrated into the genome at the LAC4 locus. *K. lactis* was prepared for electroporation by growing 100 ml of cells to an optical density of 1.0 in YPD broth (10 g yeast extract, 20 g peptone and 1% dextrose per liter). The cells were chilled on ice for 10 min then pelleted at 4° C. by centrifugation at 4000 rpm for 10 min. The pellet was washed with 100 ml sterile cold water and with 5 ml sterile cold 1 M sorbitol, then resuspended in 0.1 ml sterile cold 1 M sorbitol to a final volume of ~0.3 ml. The cells were stored on ice until use. To electroporate DNA into the prepared cells, 70 μl of *K. lactis* cell suspension was mixed with 10 μl of purified SacII digested expression vector. The mixture was placed into a cold 0.2 cm electroporation cuvette and a pulse of electricity (1.5 KV, 25 pF and 200 Ohm) was applied to the cell mixture. The cells were immediately diluted with 1 ml sterile cold 1 M sorbitol and placed on ice for 10 min after which 1 ml of YPD was added and the cells grown at 30° C. for 2h. Cells were plated on YPD agar plates containing 200 μg/ml G418 and colonies of integrants allowed to form by incubation at 30° C. for 3 days. Secretion of EK-CBD(W 275F) was achieved by growing integrants in YPD broth for 24–96 h. Enterokinase proteolytic activity associated with secreted EK-CBD (W275F) was assayed directly from culture medium in a fluorogenic assay as follows: 50 μl of culture supernatant was mixed with 50 μl of 2× assay buffer (875 μM fluorescent peptide (H-Gly-Asp-Asp-Asp-Asp-Lys-BNA (SEQ ID NO:44)), 17.6% DMSO, 125 mM Tris pH 8.0) and incubated at RT for 5–30 min. Released fluorescence compared to a standard reaction (50 µl YPD and 50 µl 2× assay buffer) was measured with a Perkin Elmer (Emeryville, Calif.) LS50B Luminescence Spectrophotometer with excitation and emission wavelengths of 337 nm and 420 nm, respectively.

EXAMPLE IX

Chitin Bead Affinity Purification of EK-CBD(W275F) Activity

EK-CBD(W275F) was purified directly from culture media using a batch method as follows: a 250 ml YPD-broth culture of a *K. lactis* EK-CBD(W275F) secreting strain was grown at 30° C. for 48 h. The culture was cleared of cells by centrifugation at 4000 rpm for 10 min at 4° C. Cleared culture was adjusted to 2 M NaCl by addition of 29.22 g of solid NaCl to promote binding of EK-CBD(W 275F) to chitin beads. New England Biolabs (Beverly, Mass.) chitin bead suspension (5 ml) was added to the cleared culture and the beads were gently stirred for 2 hours at 4° C. The entire mixture was passed through an empty 23 cm×2.3 cm column to collect the EK-CBD(W275F)-bound chitin beads. Collected beads were washed by passing 75 ml of wash buffer (2 M NaCl, 20 mM Tris pH 7.4) through the column. EK-CBD(W275F) was eluted from the chitin beads by passing 25 ml of elution buffer (50 mM NaCl, 20 mM Tris pH 7.4) through the column while collecting 0.5 ml fractions. Fractions were assayed for enterokinase activity as follows: 50 µl of a fraction was mixed with 50 µl of 2× assay buffer (875 µM fluorescent peptide (H-Gly-Asp-Asp-Asp-Asp-Lys-BNA) (SEQ ID NO:45), 17.60% DMSO, 125 mM Tris pH 8.0) and incubated at RT for 5–30 min. Released fluorescence compared to a standard reaction (50 µl elution buffer and 50 µl 2× assay buffer) was measured with a Perkin Elmer (Emeryville, Calif.) LS50B Luminescence Spectrophotometer with excitation and emission wavelengths of 337 nm and 420 nm, respectively. Fractions having activity were pooled and stored frozen at −20° C.

Although certain preferred embodiments of the present invention have been described, the spirit and scope of the invention is by no means restricted to what is described above. For example, within the general method for secreting CBD-tagged enterokinase, it is also possible to express and purify other CBD-tagged proteins from both *K. lactis* as well as from other yeast and fungi, or from other eukaryotic or prokaryotic secretory or cytosolic expression systems.

What is claimed is:

1. A method for producing and purifying a target protein molecule comprising:
   (a) constructing a DNA expression vector which expresses a hybrid polypeptide in a transformed host cell, the hybrid polypeptide comprising the target protein molecule and a modified chitin binding domain (CBD) that has a specific and reversible affinity for a substrate under non-denaturing conditions, wherein the non-denaturing conditions are selected from the group consisting of non-denaturing ionic conditions, non-denaturing pH, and non-denaturing detergent concentration;
   (b) introducing the expression vector into an appropriate host cell and expressing the hybrid polypeptide;
   (c) contacting the hybrid polypeptide produced by the transformed cell with the substrate to which the CBD binds; and
   (d) recovering the hybrid polypeptide.

2. The method of claim 1, wherein recovery of the hybrid polypeptide further comprises:
   contacting the bound hybrid polypeptide with a substance which displaces the hybrid polypeptide.

3. A method according to claim 1, wherein the altered non-denaturing ionic condition is a reduction in NaCl molarity from a salt concentration of 2M NaCl to a salt concentration in the range of 0–1M NaCl.

4. A method according to claim 1, wherein the substrate is chitin.

5. A method for purifying a chitin binding domain-target molecule conjugate from a mixture of molecules in a preparation comprising:

(a) adding to the preparation, a substrate to which chitin binding domain (CDB) binds with a specific and reversible affinity under non-denaturing conditions, wherein the non-denaturing conditions are selected from the group consisting of non-denaturing ionic conditions, non-denaturing pH, and non-denaturing detergent concentration, so as to permit binding and immobilizing of the chitin binding domain-target molecule conjugate to the substrate;

(b) removing the bound chitin binding domain-target molecule conjugate from the mixture into a buffer; and (c) recovering the purified chitin binding domain-target molecule conjugate.

6. A method according to claim 5, wherein the altered non-denaturing ionic conditions comprise a reduction in NaCl molarity from a salt concentration of 2M NaCl to a salt concentration in the range of 0–1M NaCl.

7. A method according to claim 5, wherein the substrate is chitin.

* * * * *

SEQUENCE LISTING

```
<160> NUMBER OF SEQ ID NOS: 49

<210> SEQ ID NO 1
<211> LENGTH: 45
<212> TYPE: PRT
<213> ORGANISM: Unknown
<220> FEATURE:
<223> OTHER INFORMATION: chitin binding domain of Bacillus circulans
      WL-12 chitinase A1

<400> SEQUENCE: 1

Ala Trp Gln Val Asn Thr Ala Tyr Thr Ala Gly Gln Leu Val Thr Tyr
1               5                   10                  15

Asn Gly Lys Thr Tyr Lys Cys Leu Gln Pro His Thr Ser Leu Ala Gly
            20                  25                  30

Trp Glu Pro Ser Asn Val Pro Ala Leu Trp Gln Leu Gln
        35                  40                  45

<210> SEQ ID NO 2
<211> LENGTH: 47
<212> TYPE: PRT
<213> ORGANISM: unknown
<220> FEATURE:
<223> OTHER INFORMATION: chitin binding domain of Bacillus circulans
      WL-12 chitinase D

<400> SEQUENCE: 2

Ala Ala Gln Trp Gln Ala Gly Thr Ala Tyr Lys Gln Gly Asp Leu Val
1               5                   10                  15

Thr Tyr Leu Asn Lys Asp Tyr Glu Cys Ile Gln Pro His Thr Ala Leu
            20                  25                  30

Thr Gly Trp Glu Pro Ser Asn Val Pro Ala Leu Trp Lys Tyr Val
        35                  40                  45

<210> SEQ ID NO 3
<211> LENGTH: 52
```

```
<212> TYPE: PRT
<213> ORGANISM: unknown
<220> FEATURE:
<223> OTHER INFORMATION: chitin binding domain of Aeromonas sp. Strain
      10S-24 chitinase II

<400> SEQUENCE: 3

Pro Gly Gly Cys Ala Ala Trp Ala Glu Gly Asn Thr Tyr Thr Ala Gly
1               5                   10                  15

Thr Cys Ala Ser Tyr Gly Gly Lys Asp Tyr Val Ala Gln Val Thr His
            20                  25                  30

Thr Ala Tyr Val Gly Ala Asn Trp Asn Pro Ala Ala Thr Pro Thr Leu
        35                  40                  45

Trp Lys Leu Lys
    50

<210> SEQ ID NO 4
<211> LENGTH: 56
<212> TYPE: PRT
<213> ORGANISM: unknown
<220> FEATURE:
<223> OTHER INFORMATION: chitin binding domain of Janthinobacterium
      lividum chitinase

<400> SEQUENCE: 4

Val Ala Cys Val Pro Trp Gln Glu Gly Gly Val Thr Tyr Asn Ala Gly
1               5                   10                  15

Thr Val Thr Tyr Leu Gly Gly Asn Tyr Thr Ala Leu Val Thr Gln Thr
            20                  25                  30

Asp His Val Gly Ser Gly Trp Asn Pro Val Ser Thr Pro Ser Leu Trp
        35                  40                  45

Ala Gly Gly Thr Val Asp Gly Gly
    50                  55

<210> SEQ ID NO 5
<211> LENGTH: 51
<212> TYPE: PRT
<213> ORGANISM: unknown
<220> FEATURE:
<223> OTHER INFORMATION: chitin binding domain of Serratia marcescens
      2170 chitinase C

<400> SEQUENCE: 5

Asp Pro Gly Ala Pro Glu Trp Gln Asn Asn His Ser Tyr Lys Ala Gly
1               5                   10                  15

Asp Val Val Ser Tyr Lys Gly Lys Lys Tyr Thr Cys Ile Gln Ala His
            20                  25                  30

Thr Ser Asn Ala Gly Trp Thr Pro Asp Ala Ala Phe Thr Leu Trp Gln
        35                  40                  45

Leu Ile Ala
    50

<210> SEQ ID NO 6
<211> LENGTH: 47
<212> TYPE: PRT
<213> ORGANISM: unknown
<220> FEATURE:
<223> OTHER INFORMATION: chitin binding domain of Aeromonas sp.
      Strain 10S-24 chitinase II

<400> SEQUENCE: 6

Ala Pro Val Trp Ser Ser Ser Thr Ala Tyr Asn Gly Gly Trp Gln Val
1               5                   10                  15
```

-continued

Ser Tyr Asn Gly His Thr Tyr Thr Ala Lys Trp Trp Thr Gln Gly Asn
                20                  25                  30

Val Pro Ser Ser Ser Thr Gly Asp Gly Ser Pro Trp Asn Asp Val
            35                  40                  45

<210> SEQ ID NO 7
<211> LENGTH: 47
<212> TYPE: PRT
<213> ORGANISM: unknown
<220> FEATURE:
<223> OTHER INFORMATION: chitin binding domain of Aeromonas sp.
      Strain 10S ORF1

<400> SEQUENCE: 7

Ala Ala Thr Trp Ser Ser Ser Thr Ala Tyr Asn Gly Gly Ala Thr Val
1               5                   10                  15

Ala Tyr Asn Gly His Asn Tyr Gln Ala Lys Trp Trp Thr Gln Gly Asn
                20                  25                  30

Val Pro Ser Ser Ser Thr Gly Asp Gly Gln Pro Trp Ala Asp Leu
            35                  40                  45

<210> SEQ ID NO 8
<211> LENGTH: 47
<212> TYPE: PRT
<213> ORGANISM: unknown
<220> FEATURE:
<223> OTHER INFORMATION: chitin binding domain of Aeromonas sp.
      Strain 10S-24 chitinase I

<400> SEQUENCE: 8

Ala Pro Val Trp Ser Ser Ser Thr Ala Tyr Asn Gly Gly Trp Gln Val
1               5                   10                  15

Ser Tyr Asn Gly His Thr Tyr Thr Ala Lys Trp Trp Thr Gln Gly Asn
                20                  25                  30

Val Pro Ser Ser Ser Thr Gly Asp Gly Ser Pro Trp Asn Asp Val
            35                  40                  45

<210> SEQ ID NO 9
<211> LENGTH: 48
<212> TYPE: PRT
<213> ORGANISM: unknown
<220> FEATURE:
<223> OTHER INFORMATION: chitin binding domain of Serratia marcescens
      2170 chitinase B

<400> SEQUENCE: 9

Ala Pro Ala Tyr Tyr Val Pro Gly Thr Thr Tyr Ala Gln Gly Ala Leu
1               5                   10                  15

Val Ser Tyr Gln Gly Tyr Val Trp Gln Thr Lys Trp Gly Tyr Ile Thr
                20                  25                  30

Ser Ala Pro Gly Ser Asp Ser Ala Trp Leu Lys Val Gly Arg Leu Ala
            35                  40                  45

<210> SEQ ID NO 10
<211> LENGTH: 53
<212> TYPE: PRT
<213> ORGANISM: unknown
<220> FEATURE:
<223> OTHER INFORMATION: chitin binding domain of Janthinobacterium
      lividum chitinase

<400> SEQUENCE: 10

Gly Thr Cys Ala Leu Ala Trp Ala Ala Gly Thr Ala Tyr Ser Ala Gly

```
                1               5                   10                  15
Ala Thr Val Ser Tyr Ala Gly Thr Asn Tyr Arg Ala Asn Tyr Trp Thr
                            20                  25                  30

Gln Gly Asp Asn Pro Ser Thr Ser Ser Gly Gly Ala Gly Thr Gly Lys
            35                  40                  45

Pro Trp Thr Ser Gln
        50
```

<210> SEQ ID NO 11
<211> LENGTH: 48
<212> TYPE: PRT
<213> ORGANISM: unknown
<220> FEATURE:
<223> OTHER INFORMATION: chitin binding domain of Alteromonas sp. Strain
      O-7 chitinase 85

<400> SEQUENCE: 11

```
Gly Ala Glu Tyr Pro Thr Trp Asp Arg Ser Thr Val Tyr Val Gly Gly
1               5                   10                  15

Asp Arg Val Ile His Asn Ser Asn Val Leu Glu Ala Lys Trp Trp Thr
            20                  25                  30

Gln Gly Glu Glu Pro Gly Thr Ala Asp Val Trp Lys Ala Val Thr Asn
            35                  40                  45
```

<210> SEQ ID NO 12
<211> LENGTH: 48
<212> TYPE: PRT
<213> ORGANISM: unknown
<220> FEATURE:
<223> OTHER INFORMATION: chitin binding domain of Streptomyces griseus
      chitinase C

<400> SEQUENCE: 12

```
Ala Thr Cys Ala Thr Ala Trp Ser Ser Ser Val Tyr Thr Asn Gly
1               5                   10                  15

Gly Thr Val Ser Tyr Asn Gly Arg Asn Tyr Thr Ala Lys Trp Trp Thr
            20                  25                  30

Gln Asn Glu Arg Pro Gly Thr Ser Asp Val Trp Ala Asp Lys Gly Ala
            35                  40                  45
```

<210> SEQ ID NO 13
<211> LENGTH: 46
<212> TYPE: PRT
<213> ORGANISM: unknown
<220> FEATURE:
<223> OTHER INFORMATION: chitin binding domain of Vibrio harveyi
      chitinase A

<400> SEQUENCE: 13

```
Ala Ala Ala Trp Asp Ala Asn Thr Val Tyr Val Glu Gly Asp Gln Val
1               5                   10                  15

Ser His Asp Gly Ala Thr Trp Val Ala Gly Trp Tyr Thr Arg Gly Glu
            20                  25                  30

Glu Pro Gly Thr Thr Gly Glu Trp Gly Val Lys Lys Ala Ser
            35                  40                  45
```

<210> SEQ ID NO 14
<211> LENGTH: 51
<212> TYPE: PRT
<213> ORGANISM: unknown
<220> FEATURE:
<223> OTHER INFORMATION: chitin binding domain of Aeromonas caviae
      extracellular chitinase A

<400> SEQUENCE: 14

Gln Val Gln Leu Gly Trp Asp Ala Gly Val Val Tyr Asn Gly Gly Asp
1               5                   10                  15

Val Thr Ser His Asn Gly Arg Lys Trp Lys Ala Gln Tyr Trp Thr Lys
            20                  25                  30

Gly Asp Glu Pro Gly Lys Ala Ala Val Trp Val Asp Gln Gly Ala Ala
        35                  40                  45

Ser Cys Asn
    50

<210> SEQ ID NO 15
<211> LENGTH: 12
<212> TYPE: DNA
<213> ORGANISM: unknown
<220> FEATURE:
<223> OTHER INFORMATION: oligonucleotide sequence

<400> SEQUENCE: 15
atcgagggta gg                                                                12

<210> SEQ ID NO 16
<211> LENGTH: 4
<212> TYPE: PRT
<213> ORGANISM: unknown
<220> FEATURE:
<223> OTHER INFORMATION: amino acid of SEQ ID NO:15

<400> SEQUENCE: 16

Ile Glu Gly Arg
1

<210> SEQ ID NO 17
<211> LENGTH: 28
<212> TYPE: DNA
<213> ORGANISM: unknown
<220> FEATURE:
<223> OTHER INFORMATION: primer

<400> SEQUENCE: 17
ctcgagcata tggcacccgc ccgctcgc                                                28

<210> SEQ ID NO 18
<211> LENGTH: 40
<212> TYPE: DNA
<213> ORGANISM: unknown
<220> FEATURE:
<223> OTHER INFORMATION: primer

<400> SEQUENCE: 18
cgtggttgct cttccgcact cctggactgg ctcccagcag                                   40

<210> SEQ ID NO 19
<211> LENGTH: 20
<212> TYPE: DNA
<213> ORGANISM: unknown
<220> FEATURE:
<223> OTHER INFORMATION: primer

<400> SEQUENCE: 19
agatgcacta gttgccctac                                                         20

<210> SEQ ID NO 20
<211> LENGTH: 44

<212> TYPE: DNA
<213> ORGANISM: unknown
<220> FEATURE:
<223> OTHER INFORMATION: primer

<400> SEQUENCE: 20
tgtacgctgc agttacaagc ttgtgtgggg ctgcaaacat ttat             44

<210> SEQ ID NO 21
<211> LENGTH: 59
<212> TYPE: DNA
<213> ORGANISM: unknown
<220> FEATURE:
<223> OTHER INFORMATION: oligonucleotide

<400> SEQUENCE: 21
agcttggcag gatttgaacc atccaacgtt cctgccttgt ggcagcttca ataactgca      59

<210> SEQ ID NO 22
<211> LENGTH: 59
<212> TYPE: DNA
<213> ORGANISM: unknown
<220> FEATURE:
<223> OTHER INFORMATION: oligonucleotide

<400> SEQUENCE: 22
agcttggcag gagccgaacc atccaacgtt cctgccttgg cccagcttca ataactgca      59

<210> SEQ ID NO 23
<211> LENGTH: 58
<212> TYPE: DNA
<213> ORGANISM: unknown
<220> FEATURE:
<223> OTHER INFORMATION: oligonucleotide

<400> SEQUENCE: 23
agcttggcag gatttgaacc accaacgttc ctgccttgtt tcagcttcaa taactgca       58

<210> SEQ ID NO 24
<211> LENGTH: 58
<212> TYPE: DNA
<213> ORGANISM: unknown
<220> FEATURE:
<223> OTHER INFORMATION: oligonucleotide

<400> SEQUENCE: 24
agcttggcag gaaccgaacc atccaacgtt ctgccttgtg gcagcttcaa taactgca       58

<210> SEQ ID NO 25
<211> LENGTH: 59
<212> TYPE: DNA
<213> ORGANISM: unknown
<220> FEATURE:
<223> OTHER INFORMATION: oligonucleotide

<400> SEQUENCE: 25
agcttggcag gatatgaacc atccaacgtt cctgccttgt ggcagcttca ataactgca      59

<210> SEQ ID NO 26
<211> LENGTH: 59
<212> TYPE: DNA
<213> ORGANISM: unknown
<220> FEATURE:
<223> OTHER INFORMATION: oligonucleotide

<400> SEQUENCE: 26

-continued agcttggcag gatgggaagc ctccaacgtt cctgccttgt ggcagcttca ataactgca      59

<210> SEQ ID NO 27
<211> LENGTH: 59
<212> TYPE: DNA
<213> ORGANISM: unknown
<220> FEATURE:
<223> OTHER INFORMATION: oligonucleotide

<400> SEQUENCE: 27
agcttggcag gatgggaatt ttccaacgtt cctgccttgt ggcagcttca ataactgca      59

<210> SEQ ID NO 28
<211> LENGTH: 59
<212> TYPE: DNA
<213> ORGANISM: unknown
<220> FEATURE:
<223> OTHER INFORMATION: oligonucleotide

<400> SEQUENCE: 28
agcttggcag gatgggaacc atccaacgtt gccgccttgt ggcagcttca ataactgca      59

<210> SEQ ID NO 29
<211> LENGTH: 56
<212> TYPE: DNA
<213> ORGANISM: unknown
<220> FEATURE:
<223> OTHER INFORMATION: oligonucleotide

<400> SEQUENCE: 29
agcttggcag gatgggaacc atccaacgtt gccttgtggc agcttcaata actgca         56

<210> SEQ ID NO 30
<211> LENGTH: 59
<212> TYPE: DNA
<213> ORGANISM: unknown
<220> FEATURE:
<223> OTHER INFORMATION: oligonucleotide

<400> SEQUENCE: 30
agcttggcag gatgggaacc atccaacgtt cctgccttgt ttcagcttca ataactgca      59

<210> SEQ ID NO 31
<211> LENGTH: 75
<212> TYPE: DNA
<213> ORGANISM: unknown
<220> FEATURE:
<223> OTHER INFORMATION: oligonucleotide

<400> SEQUENCE: 31
ccggtctgaa ctcaggcctc acgacaaatc ctggtgtatc cgctgcccag gtcaacacag      60
cttatactgc gggac                                                      75

<210> SEQ ID NO 32
<211> LENGTH: 75
<212> TYPE: DNA
<213> ORGANISM: unknown
<220> FEATURE:
<223> OTHER INFORMATION: oligonucleotide

<400> SEQUENCE: 32
ccggtctgaa ctcaggcctc acgacaaatc ctggtgtatc cgcttttcag gtcaacacag      60
cttatactgc gggac                                                      75

```
<210> SEQ ID NO 33
<211> LENGTH: 50
<212> TYPE: DNA
<213> ORGANISM: unknown
<220> FEATURE:
<223> OTHER INFORMATION: oligonucleotide

<400> SEQUENCE: 33
aattggtcac atataacggc aagacgtata aatgtttgca gcccgccaca          50

<210> SEQ ID NO 34
<211> LENGTH: 50
<212> TYPE: DNA
<213> ORGANISM: unknown
<220> FEATURE:
<223> OTHER INFORMATION: oligonucleotide

<400> SEQUENCE: 34
aattggtcac atataacggc aagacgtata aatgtttgca gcccttttaca         50

<210> SEQ ID NO 35
<211> LENGTH: 50
<212> TYPE: DNA
<213> ORGANISM: unknown
<220> FEATURE:
<223> OTHER INFORMATION: oligonucleotide

<400> SEQUENCE: 35
aattggtcac atataacggc aagacgtata aatgtttgca gccccacgca          50

<210> SEQ ID NO 36
<211> LENGTH: 16
<212> TYPE: DNA
<213> ORGANISM: unknown
<220> FEATURE:
<223> OTHER INFORMATION: oligonucleotide

<400> SEQUENCE: 36
ctagtgcccg ggccaa                                              16

<210> SEQ ID NO 37
<211> LENGTH: 59
<212> TYPE: DNA
<213> ORGANISM: unknown
<220> FEATURE:
<223> OTHER INFORMATION: oligonucleotide

<400> SEQUENCE: 37
agcttggcag gatatgaacc atccaacgtt cctgccttgt ggcagcttca ataactgca   59

<210> SEQ ID NO 38
<211> LENGTH: 36
<212> TYPE: DNA
<213> ORGANISM: unknown
<220> FEATURE:
<223> OTHER INFORMATION: primer

<400> SEQUENCE: 38
ggctcttcca tgcggagact gctgcaggaa acggag                        36

<210> SEQ ID NO 39
<211> LENGTH: 39
<212> TYPE: DNA
<213> ORGANISM: unknown
<220> FEATURE:
<223> OTHER INFORMATION: primer
```

-continued

```
<400> SEQUENCE: 39
ggctcttccg ccgccctgct ggggtaccag atactcctc                              39

<210> SEQ ID NO 40
<211> LENGTH: 39
<212> TYPE: DNA
<213> ORGANISM: unknown
<220> FEATURE:
<223> OTHER INFORMATION: primer

<400> SEQUENCE: 40
ccgctcgaga aagaattgt tggtggttct gattctaga                               39

<210> SEQ ID NO 41
<211> LENGTH: 65
<212> TYPE: DNA
<213> ORGANISM: unknown
<220> FEATURE:
<223> OTHER INFORMATION: primer

<400> SEQUENCE: 41
ataagaatgc ggccgctcat tgaagctgcc acaaggcagg aacgttggat ggttcaaatc       60
ctgcc                                                                   65

<210> SEQ ID NO 42
<211> LENGTH: 39
<212> TYPE: DNA
<213> ORGANISM: unknown
<220> FEATURE:
<223> OTHER INFORMATION: primer

<400> SEQUENCE: 42
tccgagctca aaacaatgag atttccttca atttttact                              39

<210> SEQ ID NO 43
<211> LENGTH: 21
<212> TYPE: DNA
<213> ORGANISM: unknown
<220> FEATURE:
<223> OTHER INFORMATION: primer

<400> SEQUENCE: 43
gcatgtatac atcagtatct c                                                 21

<210> SEQ ID NO 44
<211> LENGTH: 6
<212> TYPE: PRT
<213> ORGANISM: unknown
<220> FEATURE:
<223> OTHER INFORMATION: fluorescent peptide

<400> SEQUENCE: 44

Gly Asp Asp Asp Asp Lys
1               5

<210> SEQ ID NO 45
<211> LENGTH: 15
<212> TYPE: DNA
<213> ORGANISM: unknown
```

-continued

```
<220> FEATURE:
<223> OTHER INFORMATION: polypeptide

<400> SEQUENCE: 45
gatgacgatg acaag                                                15

<210> SEQ ID NO 46
<211> LENGTH: 5
<212> TYPE: PRT
<213> ORGANISM: unknown
<220> FEATURE:
<223> OTHER INFORMATION: amino acid of SEQ ID NO:45

<400> SEQUENCE: 46

Asp Asp Asp Asp Lys
1               5

<210> SEQ ID NO 47
<211> LENGTH: 19
<212> TYPE: DNA
<213> ORGANISM: unknown
<220> FEATURE:
<223> OTHER INFORMATION: polypeptide

<400> SEQUENCE: 47
ccgggtgcgg cacactcac                                            19

<210> SEQ ID NO 48
<211> LENGTH: 6
<212> TYPE: PRT
<213> ORGANISM: unknown
<220> FEATURE:
<223> OTHER INFORMATION: amino acid of SEQ ID NO:47

<400> SEQUENCE: 48

Pro Gly Ala Ala His Tyr
1               5

<210> SEQ ID NO 49
<211> LENGTH: 30
<212> TYPE: DNA
<213> ORGANISM: unknown
<220> FEATURE:
<223> OTHER INFORMATION: polyasparagine linker

<400> SEQUENCE: 49
aacaacaaca acaacaacaa caacaacaac                                30
```